(12) United States Patent
Dayton et al.

(10) Patent No.: US 7,358,226 B2
(45) Date of Patent: Apr. 15, 2008

(54) ULTRASONIC CONCENTRATION OF DRUG DELIVERY CAPSULES

(75) Inventors: Paul Dayton, Davis, CA (US); Katherine W. Ferrara, Davis, CA (US); Michaelann Shortencarier, Sacramento, CA (US); Susannah Bloch, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 170 days.

(21) Appl. No.: 10/928,648

(22) Filed: Aug. 26, 2004

(65) Prior Publication Data

US 2005/0084538 A1 Apr. 21, 2005

Related U.S. Application Data

(60) Provisional application No. 60/498,405, filed on Aug. 27, 2003.

(51) Int. Cl.
| | |
|---|---|
| A61B 8/00 | (2006.01) |
| A61K 38/08 | (2006.01) |
| A61K 38/13 | (2006.01) |
| A61K 31/445 | (2006.01) |
| A61K 31/277 | (2006.01) |
| A61K 31/138 | (2006.01) |
| A61K 9/127 | (2006.01) |
| A61K 9/133 | (2006.01) |

(52) U.S. Cl. ................ 514/2; 424/9.5; 424/9.51; 424/9.52; 424/130.1; 424/450; 424/812; 514/15; 514/225.5; 514/573; 514/731; 514/741

(58) Field of Classification Search ............. 424/9.321, 424/9.51, 9.52
See application file for complete search history.

(56) References Cited

U.S. PATENT DOCUMENTS

| | | | |
|---|---|---|---|
| 4,235,871 A | 11/1980 | Papahadjopoulos et al. | |
| 4,265,251 A | 5/1981 | Tickner | |
| 4,442,843 A | 4/1984 | Rasor et al. | |
| 4,533,254 A | 8/1985 | Cook et al. | |
| 4,572,203 A | 2/1986 | Feinstein | |
| 4,657,756 A | 4/1987 | Rasor et al. | |
| 4,681,199 A | 7/1987 | Maucher et al. | |
| 5,088,499 A | 2/1992 | Unger | |
| 5,147,631 A | 9/1992 | Glajch et al. | |
| 5,190,766 A * | 3/1993 | Ishihara | 424/489 |
| 5,228,446 A | 7/1993 | Unger et al. | |
| 5,271,928 A | 12/1993 | Schneider et al. | |
| 5,380,519 A | 1/1995 | Schneider et al. | |
| 5,413,774 A | 5/1995 | Schneider et al. | |
| 5,469,854 A * | 11/1995 | Unger et al. | 600/458 |
| 5,527,521 A | 6/1996 | Unger | |
| 5,531,980 A | 7/1996 | Schneider et al. | |
| 5,547,656 A | 8/1996 | Unger | |
| 5,558,092 A | 9/1996 | Unger et al. | |
| 5,558,094 A | 9/1996 | Quay | |
| 5,573,751 A | 11/1996 | Quay | |
| 5,580,575 A * | 12/1996 | Unger et al. | 424/450 |
| 5,585,112 A | 12/1996 | Unger et al. | |
| 5,620,689 A | 4/1997 | Allen et al. | |
| 5,715,824 A | 2/1998 | Unger et al. | |
| 5,769,080 A | 6/1998 | Unger et al. | |
| 5,770,222 A | 6/1998 | Unger et al. | |
| 5,935,553 A * | 8/1999 | Unger et al. | 424/9.51 |
| 6,146,657 A | 11/2000 | Unger et al. | |
| 6,245,747 B1 * | 6/2001 | Porter et al. | 514/44 |
| 6,352,683 B1 * | 3/2002 | ten Cate | 424/9.34 |
| 6,416,740 B1 | 7/2002 | Unger | |
| 6,443,898 B1 | 9/2002 | Unger et al. | |
| 6,475,148 B1 | 11/2002 | Jackson et al. | |
| 2002/0071843 A1 | 6/2002 | Li et al. | |
| 2002/0102215 A1 | 8/2002 | Klaveness et al. | |
| 2002/0150539 A1 | 10/2002 | Unger | |
| 2002/0151792 A1 | 10/2002 | Conston et al. | |
| 2002/0197210 A1 | 12/2002 | Bednarski et al. | |
| 2003/0003055 A1 * | 1/2003 | Unger et al. | 424/9.51 |
| 2003/0039613 A1 | 2/2003 | Unger et al. | |
| 2003/0044354 A1 | 3/2003 | Carpenter, Jr. et al. | |
| 2003/0143161 A1 * | 7/2003 | Kawabata et al. | 424/9.52 |
| 2003/0157025 A1 * | 8/2003 | Unger et al. | 424/9.52 |
| 2003/0215394 A1 * | 11/2003 | Short et al. | 424/9.52 |
| 2004/0059313 A1 * | 3/2004 | Tachibana et al. | 604/500 |
| 2004/0267234 A1 * | 12/2004 | Heart et al. | 604/500 |

FOREIGN PATENT DOCUMENTS

| | | |
|---|---|---|
| EP | 0727225 A2 | 8/1996 |
| WO | WO 96/40285 | 12/1996 |
| WO | WO 99/65467 | 12/1999 |
| WO | WO 03/034975 * | 5/2003 |
| WO | WO 03/034975 A2 | 5/2003 |

OTHER PUBLICATIONS

Kost et al. "Ultrasound-enhanced Polymer Degradation and Release of Incorporated Substances," Proc. Natl. Acad. Sci. USA, 1989, 86, 7663-7666.*

(Continued)

*Primary Examiner*—Johann R. Richter
*Assistant Examiner*—James H Alstrum-Acevedo
(74) *Attorney, Agent, or Firm*—Fenwick & West LLP

(57) ABSTRACT

Methods, compositions and apparatus for localized delivery of compounds are provided. In certain embodiments, radiation force is used to direct carriers to a target site, and additional radiation is used to fragment the localized carriers, releasing associate compounds. Ultrasound radiation is preferred as the source for radiation force and for fragmentation. Also encompassed are embodiments in which targeting and fragmentations are combined with imaging of the treatment site. Alternate embodiments are disclosed in which compounds are locally delivered without use of carriers.

51 Claims, 11 Drawing Sheets

OTHER PUBLICATIONS

Apfel, R. E., et al., "Gauging the Likelihood of Cavitation from Short-Pulse, Low-Duty Cycle Diagnostic Ultrasound," *Ultrasound in Medicine and Biology*, 1991, pp. 179-185, vol. 17, No. 2, Pergamon Press.

Bartus, R. T., et al., "Intravenous Cereport (RMP-7) Modifies Topographic Uptake Profile of Carboplatin within Rat Giloma and Brain Surrounding Tumor, Elevates Platinum Levels, and Enhances Survival," *Journal of Pharmacology and Experimental Therapeutics*, Jun. 2000, pp. 903-911, vol. 293, No. 3, The American Society for Pharmacology and Experimental Therapeutics.

Dayton, P. A., et al., "Acoustic Radiation Force In Vivo: A Mechanism to Assist Targeting of Microbubbles," *Ultrasound in Medicine & Biology*, 1999, pp. 1195-1201, vol. 25, No. 8, World Federation for Ultrasound in Medicine & Biology.

Dayton, P. A., et al. "The Magnitude of Radiation Force on Ultrasound Contrast Agents," *Journal of the Acoustical Society of America*, Nov. 2002, pp. 2183-2192, vol. 112, No. 5, Acoustical Society of America.

Dayton, P. A., et al., "A Preliminary Evaluation of the Effects of Primary and Secondary Radiation Forces on Acoustic Contrast Agents," *IEEE Transactions on Ultrasonics, Ferroelectrics, and Frequency Control*, Nov. 1997, pp. 1264-1277, vol. 44, No. 6, IEEE.

Demos, S. M., et al., "In Vivo Targeting of Acoustically Reflective Liposomes for Intravascular and Transvascular Ultrasonic Enhancement," *Journal of the American College of Cardiology*, 1999, pp. 867-875, vol. 33, Elsevier Science Inc.

Hurst, R. D., et al., "Nitric Oxide-Induced Pertubations in a Cell Culture Model of the Blood-Brain Barrier," *Journal of Cellular Physiology*, Apr. 1996, pp. 89-94, vol. 167, No. 1, Wiley-Liss, Inc.

Janzer, R. C., et al., "Astrocytes Induce Blood-Brain Barrier Properties in Endothelial Cells," *Nature*, Jan. 15-21, 1987, pp. 253-257, vol. 325, No. 6101.

Langer, R., "Drug Delivery and Targeting," *Nature*, Apr. 30, 1998, pp. 5-10, vol. 392 supplemental.

Lian, T., et al., "Trends and Developments in Liposome Drug Delivery Systems," *Journal of Pharmaceutical Sciences*, Jun. 2001, pp. 667-680, vol. 90, No. 6, Wiley-Liss, Inc. and the American Pharmaceutical Association.

Linder, J. R., "Evolving Applications for Contrast Ultrasound," *American Journal of Cardiology*, Nov. 18, 2002, pp. 72J-80J, vol. 90, No. 10A, Excerpta Medica, Inc.

Linder, J. R., et al., "Delivery of Drugs with Ultrasound," *Echocardiography: A Journal of CV Ultrasound & Allied Technology*, 2001, pp. 329-337, vol. 18, No. 4.

May, D. J., et al., "Dynamics and Fragmentation of Thick-Shelled Microbubbles," *IEEE Transactions on Ultrasonics, Ferroelectrics, and Frequency Control*, Oct. 2002, pp. 1400-1410, vol. 49, No. 10, IEEE.

May, D., et al., "Ultrasound Contrast Agents Used for Localized Drug Delivery," *IEEE Ultrasonics Symposium Proceedings*, 2000, 4 pages.

Morgan, K. E., et al., "Experimental and Theoretical Evaluation of Microbubbles Behavior: Effect of Transmitted Phase and Bubble Size," *IEEE Transactions on Ultrasonics, Ferrelectrics and Frequency Control*, Nov. 2000, pp. 1494-1509, vol. 47, No. 6, IEEE.

Price, R. J., et al., "Delivery of Colloidal Particles and Red Blood Cells to Tissue Through Microvessel Ruptures Created by Targeted Microbubble Destruction with Ultrasound," *Circulation*, Sep. 29, 1998, pp. 1264-1267, vol. 98, No. 13, American Heart Association, Inc.

Shohet, R. V., et al., "Echocardiographic Destruction of Albumin Microbubbles Directs Gene Delivery to the Myocardium," *Circulation*, 2000, pp. 2554-2556, vol. 101, American Heart Association.

Shortencarier, M. J., et al. "A Method for Radiation-Force Localized Drug Delivery Using Gas-Filled Lipospheres," *IEEE Transactions on Ultrasonics, Ferroelectrics, and Frequency Control*, Jul. 2004, pp. 821-830, vol. 51, No. 7.

Skyba, D. M., et al., "Direct In Vivo Visualization of Intravascular Destruction of Microbubbles by Ultrasound and its Local Effects on Tissue," *Circulation*, Jul. 28, 1998, pp. 290-293, vol. 98, No. 4, American Heart Association, Inc.

Takakura, Y., et al., "Macromolecular Carrier Systems for Targeted Drug Delivery: Pharmacokinetic Considerations on Biodistribution," *Pharmaceutical Research*, 1996, pp. 820-831, vol. 13, No. 6, Plenum Publishing Corporation.

Unger, E. C., et al., "Acoustically Active Liposphores Containing Paclitaxel: A New Therapeutic Ultrasound Contrast Agent," *Investigative Radiology*, Dec. 1998, pp. 886-892, vol. 33, No. 12, Lippincott Williams & Wilkins, Inc.

Unger, E. C., et al., "Ultrasound Enhances Gene Expression of Liposomal Transfection," *Investigative Radiology*, Dec. 1997, pp. 723-727, vol. 32, No. 12, Lippincott-Raven Publishers.

Ward, M., et al., "Experimental Study of the Effects of Optison Concentration on Sonopration In Vitro," *Ultrasound in Medicine and Biology*, Sep. 2000, pp. 1169-1175, vol. 26, No. 7, World Federation for Ultrasound in Medicine & Biology.

Wheatley, M. A., et al., "Ultrasound-Triggered Drug Delivery with Contrast Imaging: Effect of Microencapsulation Method," *Materials Research Society Symposium Proceedings*, 1999, pp. 113-118, vol. 550, Materials Research Society.

Wickline, S. A., et al., "Molecular Imaging, Targeted Therapeutics, and Nanoscience," *Journal of Cellular Biochemistry Supplementary*, 2002, pp. 90-97, vol. 39, Wiley-Liss, Inc.

International Search Report and Written Opinion, PCT/US04/27931, Apr. 18, 2007, 12 pages.

Kost, J. et al., "Ultrasound-Enhanced Polymer Degradation and Release of Incorporated Substances," *Proc. Natl. Acad. Sci. USA*, Oct. 1989, pp. 7663-7666, vol. 86.

\* cited by examiner

ULTRASONIC CONCENTRATION OF DRUG DELIVERY CAPSULES

CROSS REFERENCE TO RELATED APPLICATIONS

This application claims the benefit of U.S. Provisional Application No. 60/498,405, filed Aug. 27, 2003, the entire disclosure of which is hereby incorporated by reference in its entirety for all purposes.

STATEMENT REGARDING FEDERALLY SPONSORED RESEARCH OR DEVELOPMENT

The U.S. Government has certain rights in this invention pursuant to Grant No. 2 R01 CA76062-07 awarded by the National Institutes of Health (National Cancer Institute).

BACKGROUND OF THE INVENTION

1. Field of the invention

The invention relates to methods, apparatus and compositions, useful for targeted delivery of compounds. More particularly, the invention relates to use of radiation force for targeted delivery of compounds including therapeutic agents.

2. Description of the Related Art

Ultrasound is used in medical settings as a diagnostic aid for imaging internal structures. Advantages of ultrasound over other imaging forms include low cost, portability, and safety. Ultrasound contrast agents are well known in the prior art. Typically these agents comprise vesicles having diameters on the order of 10 μm or less, a gaseous core, and an oil, lipid, polymeric or proteinaceous shell. Ultrasound contrast agents improve contrast by acting as sound wave reflectors due to acoustic differences between the agents and surrounding liquid.

A variety of therapeutic uses of ultrasound also have been described. Some applications take advantage of the ability of highly intense ultrasound waves to generate heat and thus destroy structures such as tumors or blood vessels. Such methods lack specificity and can damage healthy tissue.

Other therapeutic ultrasound applications propose use of ultrasound energy to fragment carriers such as liposomes and microbubbles to localize delivery of therapeutic agents such as drugs, nucleic acids, etc. Fragmentation increases specificity by breaking the carrier into particles sufficiently small to extravasate. By focusing the ultrasound energy at a desired delivery site such as, e.g., a tumor, higher local concentrations of a therapeutic agent may be achieved. Use of acoustically active carriers permits simultaneous visualization of the carrier to aid or confirm diagnosis and localize a treatment site. Coupling diagnostic and therapeutic ultrasound modes provides the additional advantage of allowing a clinician administering treatment to confirm carrier fragmentation at a desired treatment site.

Solid tumors rely on the formation of new blood vessels, i.e., angiogenesis, to establish the blood supply necessary to support tumor volumes in excess of a few cubic millimeters. Neo-vascularized tumors have leaky capillaries as compared to normal tissues. This provides a basis for concentrating agents within tumors by administering the agents in carriers that are too large to extravasate through normal capillaries but not too large to extravasate through leaky capillaries. Ultrasound contrast materials loaded with therapeutic agents have been proposed for this purpose. For example, U.S. Pat. No. 5,558,092 describes compositions, methods and apparatus for carrying out diagnostic and therapeutic ultrasound. Contrast materials loaded with a therapeutic agent are imaged using diagnostic ultrasound waves, and once seen accumulating in a desired area, are ruptured using therapeutic ultrasonic waves to generate enhanced cavitation or the targeted release of an agent into the region.

The prior art also teaches improving specificity and reducing toxicity for therapeutic agents by targeting carriers. Targeting may involve ligand receptor interactions such as, e.g., through a monoclonal antibody or other ligand on the surface of the carrier designed to bind to an antigen expressed at the treatment site, or through charge interactions, or other mechanisms. Such interactions require the carrier and target site to approach to within a few nanometers.

The prior art has taught use of radiation force created by ultrasound energy to manipulate acoustically active carriers such as microbubbles. Such manipulations can be used to bring the carrier to the edge of a blood vessel, or slow the velocity of a carrier within a blood vessel to promote binding of the carrier to a cell or biological matrix. However, these prior art teachings have focused on the use of the carriers, including carriers with targeting agents, in a diagnostic context such as, e.g., by including a tumor-binding ligand on the carrier to enhance the ability to image tumors ultrasonically.

To date, the prior art has failed to recognize the additional benefits created by use of ultrasonic steering of targeted carriers engineered for therapeutic (cf. diagnostic) purposes. Such carriers are engineered to be acoustically active, carry compounds such as drug payloads, and optionally to have a targeting moiety. As described herein, ultrasound is used to enhance local delivery of carried compounds by bringing the carrier to the edge of a vessel, or by slowing the velocity of such carriers within a vessel to promote binding of the carrier to a cell or biological matrix. The prior art has also failed to recognize the additional benefits created by combined steering of carriers to a site using radiation force, and fragmentation to enhance release of agent from a carrier and/or extravasation. In addition, the prior art has failed to recognize the added benefits created by combined use of therapeutic ultrasound to promote tissue permeability (sonoporation), with steering and or fragmentation.

The present invention addresses these and other deficiencies of the prior art as described more fully below.

SUMMARY OF THE INVENTION

The present invention is defined by the following claims, and nothing in this section should be taken as a limitation on those claims. Disclosed herein are methods, compositions, and apparatus for targeted delivery of compounds and carriers using radiation force.

Accordingly one aspect of the invention includes methods of using radiation force to target a carrier to a site. In one aspect, the radiation force is generated using ultrasonic radiation. In another aspect, the carrier is engineered to carry a compound such as a drug payload. In another aspect, the invention includes methods in which carriers are fragmented at the site. Yet other aspects of the invention include methods that combine imaging with the above methods, as well as methods that include administering agents or radiation to affect tissue permeability or otherwise alter cell physiology at the site.

In one embodiment, the carrier includes a molecule to further improve targeting. In a preferred embodiment, the carrier is acoustically active. Exemplary embodiments include liquid and solid contrast agents containing entrapped gas, although the invention also may be practiced using a carrier having a liquid core. Any carrier may be used, provided there exists an acoustic mismatch between the carrier and the surrounding tissue or liquid. Carriers having a liquid core are preferred for targeted delivery of water-soluble agents.

In a preferred variation of the invention, targeting is accomplished using radiation force to concentrate a carrier along a vessel wall. In another preferred variation, targeting is accomplished using radiation force to reduce carrier velocity within a vessel.

In addition, the invention provides methods of targeted delivery of compounds without carriers by altering tissue permeability or cell physiology at a target site by administering agents or radiation to affect tissue permeability or otherwise modulate cell physiology at the site. In preferred embodiments the tissue comprises a vessel or a tumor. In another preferred embodiment, the administered radiation is ultrasonic radiation. In yet other preferred embodiments, the agents modulate bradykinin receptor activity or P-gp activity.

BRIEF DESCRIPTION OF THE SEVERAL VIEWS OF THE DRAWING

These and other features, aspects, and advantages of the present invention will become better understood with regard to the following description, and accompanying drawings, where:

FIG. 10*a* resting radius of 2.4 µm; FIG. 10*b* resting radius of 1.7 µm; FIG. 10*c* resting radius 1.5 µm. Center frequency 2.25 MHz; pressure 180 kPa. Transmitted waveform shown in white.

FIG. 11*a* ultrasound off. FIG. 11*b* ultrasound on.

DETAILED DESCRIPTION OF PREFERRED EMBODIMENTS

Figure 1:
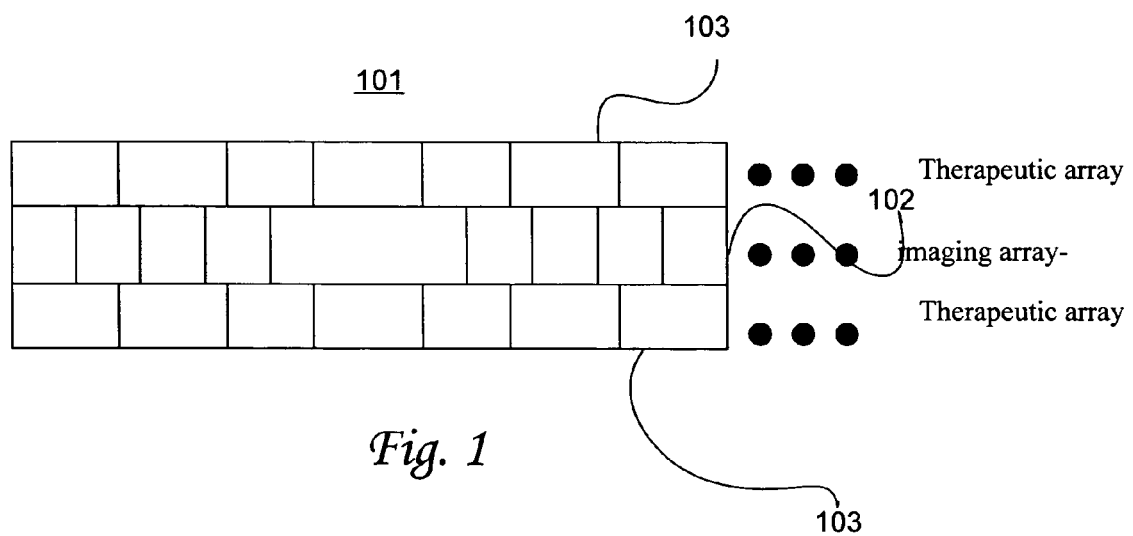
FIG. 1 is a diagram of a transducer for delivering diagnostic and therapeutic ultrasound radiation.

Briefly, and as described in more detail below, described herein are methods, compositions and apparatus for improving the efficacy and diminishing the toxicity of administered compounds. The improvements are realized by using radiation force, such as that produced by, e.g., ultrasonic radiation, to concentrate carriers at target sites, such as along vessel walls, within tumors, or at other predetermined sites. Vessels, as used herein, include any of the various tubes in which bodily fluids circulate as known in the art, e.g., veins, arteries, venules, arterioles, capillaries, and lymphatics. Once carriers have been concentrated at the target site, the carriers optionally may be disrupted to promote extravasation of carrier fragments or otherwise promote release of a compound associated with the carrier. Preferably, disruption is achieved by insonating the carrier at a frequency and pressure sufficient to fragment the carrier. The details of the parameters required to manipulate a carrier by radiation force are described further within, and with respect to a model useful for predicting carrier behavior.

Several features of the current approach should be noted. Combinations and subcombinations of various approaches involving use of radiation force to affect carrier localization or velocity in a targeted and predetermined way, fragmentation of the carrier, imaging of the carrier or of target sites, application of agents or radiation to affect tissue permeability or physiology all are contemplated to be within the scope of the present invention. In addition, the invention contemplates use of techniques to improve the specificity and reduce the toxicity of compounds by formulation with carriers. In preferred aspects of these methods of the invention, ultrasonic radiation is used to modulate vessel permeability in a targeted region, thereby promoting extravasation and absorption of the administered compound. The compounds used in this aspect of the invention may comprise any therapeutic or diagnostic substance including, by way of example but not limitation, small molecules, peptides, nucleic acids, and synthetic and semi-synthetic analogues thereof.

Advantages of this approach are numerous. Among the advantages are improved specificity and reduced toxicity for administered compounds, and improved treatment outcomes for subjects in need of treatment for a wide variety of medical conditions, especially cancers, cardiovascular diseases, and inflammatory disorders such as rheumatoid arthritis and Crohn's disease.

The invention is useful for diagnostic and or therapeutic applications in which it is beneficial to administer a compound such as, e.g., a physiologically-active compound, with or without a carrier for the purpose of diagnosing and/or treating a medical condition.

Definitions

Terms used in the claims and specification are defined as set forth below unless otherwise specified.

The term "ameliorating" refers to any therapeutically beneficial result in the treatment of a disease state or condition, e.g., a chronic or acute disease state or condition, including prophylaxis, lessening in the severity or progression, remission, or cure thereof.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to image a region.

The term "therapeutically effective amount" is an amount that is effective to ameliorate a symptom of a disease. A therapeutically effective amount can be a "prophylactically effective amount" as prophylaxis can be considered therapy.

The term "carrier" refers to any particle, such as a polymer, protein, lipid, oil, with or without a gas core, which can be concentrated with acoustic radiation force.

An "aptamer" is a type of synthetic oligonucleotide that can bind to a particular target molecule, such as a protein or metabolite.

The phrase "administering into a vessel" encompasses direct and remote administration (i.e., directly into the vessel and into a vessel that is in fluidic communication with a vessel into which agent has been directly administered).

The term "vasoporation" refers to either a mechanical increase in vascular permeability secondary to insonation with an ultrasound wave or a chemical increase in vascular permeability achieved locally by using an ultrasound wave.

It must be noted that, as used in the specification and the appended claims, the singular forms "a" "an" and "the" include plural referents unless the context clearly dictates otherwise. In addition, ranges recited are intended to be inclusive of the parameters bounding the range unless the context clearly dictates otherwise. For example, a recited range of between one and ten is intended to include one and ten unless the context clearly dictates otherwise.

Methods and Apparatus of the Invention

Background

Microcapsule drug delivery. Many oncologic drugs are toxic to normal tissues in addition to tumor cell lines. Paclitaxel, a common chemotherapeutic drug, must be solubilized in cremophore because of its low water solubility. This is undesirable as cremophore is also highly toxic. This systemic toxicity makes it desirable to deliver the antitumor agent directly to the affected area. Unger et al. *Invest. Radiol.* 33(12):886-892 (Dec. 1998) have demonstrated that paclitaxel can be suspended in a drug delivery capsule with an oil shell and that local delivery of paclitaxel can be effective against brain tumors. This drug delivery capsule is a microbubble, on order of several microns in diameter, and has a multiple layer shell that contains the compound. The mechanism of action of current microcapsule drug delivery vehicles such as Acoustively Active Lipospheres (AAL, ImaRx Therapeutics) includes injection into the bloodstream, followed by disruption at the site of interest using a high-intensity acoustic pulse. This disruption causes the contents of the capsule (the drug) to be delivered at the site of interest. Currently, this technology is in clinical trials.

Additionally, many new anti-angiogenic drugs are under development, including nine drugs currently in clinical trials that act directly on endothelial cells. These drugs inhibit endothelial cell-specific signaling or endothelial cell function, with a resulting effect on the tumor. Since a single endothelial cell supplies nutrients to many tumor cells, the inhibition of activity in a single endothelial cell has a great effect. With microcapsule drug delivery, a greater dose of drug can be delivered to endothelial cells near the tumor. In addition, investigators have shown that ultrasound in conjunction with microbubbles can result in capillary rupture in rats, with resulting extravasation of erythrocytes into the interstitial space. See, e.g., Skyba, et al., *Circulation* 98(4): 290-293 (July 1998); Price, et al., *Circulation* 98(13): 1264-1267 (September 1998). Microbubble drug delivery carriers may cause increased endothelial permeability and at the same time release a chemotherapeutic agent and so have the potential to be a powerful therapeutic tool. See, e.g., Wheatley, et al., *Mat. Res. Soc. Symp. Proc.* 550:113-118 (1999). Additionally, researchers have shown the utility of microbubble agents for gene delivery. See, e.g., Wickline and Lanza, *J. Cell. Biochem. Suppl.* 39:90-97 (2002).

Ultrasound Radiation Force—Ultrasound produces a radiation force that is exerted upon objects in a medium with an acoustic impedance different than that of the medium. An example is a microbubble in blood, although, as one of ordinary skill will recognize, ultrasound radiation forces also may be generated on non-gaseous carriers. We have shown the ability of radiation force to concentrate microbubbles in-vitro and in-vivo. Dayton, et al., *Ultrasound in Med. & Biol.*, 25(8):1195-1201(1999). An ultrasound transducer pulsing at 5 MHz center frequency, 10 kHz pulse repetition frequency ("PRF"), and 800 kPa peak pressure, has been shown to concentrate microbubbles against a vessel wall in-vivo, and reduce the velocity of these flowing agents an order of magnitude. However, to this date, the application of radiation to concentrate drug delivery carriers has not been demonstrated, nor have the combined effects of radiation force-induced concentration and carrier fragmentation.

Sonoporation—The mechanical effects of ultrasound (with and without microbubbles) to alter the permeability of cells and vessels, termed sonoporation, has now been well established. Application of ultrasound with specific acoustic parameters causes increases in cell permeability.

Ultrasonically-disrupted microcapsule drug delivery is a new idea, which is still in research trials. Initial results are promising, and this technology has the potential for significant clinical impact. Acoustic radiation force is known to act on particles in a fluid, and has recently been shown by the inventors to concentrate drug delivery carriers. The potential to concentrate drug delivery capsules at the site of interest before disruption, as described by this invention, provides a significant increase in the therapeutic efficacy of ultrasound-disrupted drug carriers. The application of ultrasound for sonoporation further contributes to the therapeutic delivery of targeted carriers such as microbubbles.

In one aspect, the invention provides ultrasound radiation force to enhance effectiveness of carriers such as acoustically active vesicles and other particles useful as carriers in the practice of the invention. Radiation force is used to "push" or concentrate carriers along the wall of a vessel. In small blood vessels, particles such as cells or carriers tend to flow along the center of the vessel, rather than along the sides. By concentrating the carriers along the vessel wall, a larger percentage of a carrier-associated compound is delivered to or through the endothelium, especially upon carrier rupture, vibration or fragmentation (generically referred to herein as fragmentation).

Additionally, the invention encompasses use of radiation force to assist delivery of targeted carriers. Targeted carriers have an adhesion mechanism incorporated into the capsule wall that is specific for a molecular signature of disease expressed on the endothelium. Since available adhesion mechanisms work on the distance of nanometers, it is important to localize the drug delivery vehicles along the vessel wall in order for such adhesion to occur. Radiation force produced perpendicular to or against the direction of flow reduces the velocity of particles flowing in a fluid. Thus, in another aspect the invention uses radiation force to assist targeted carrier delivery, since slower moving particles have a greater opportunity to interact with adhesion mechanisms on an endothelial or other surface.

The invention further encompasses use of radiation force in cooperation with ultrasonic imaging, to allow a user to observe the area being treated, and optionally with sonoporation, to increase permeability of cells in the target area. Also described in this proposal is a system specifically designed to deliver microcapsule delivery vehicles with ultrasound.

In one aspect, the invention uses ultrasound and a carrier to enhance delivery of a drug or other agent at the desired site in the following preferred manners:

1. Ultrasound e.g., at center frequencies about 0.1 MHz-40 MHz, and at a low acoustic pressure e.g., at about 20 kPa-6 MPa, and a long pulse length (e.g., about >10 cycles) or a short pulse length (e.g., about <10 cycles) and high pulse repetition frequency (e.g., about >500 Hz) to produce radiation force and concentrate carriers. The specific parameters will depend on the choice of carrier, as detailed further below, and can be readily determined by ordinarily skilled artisans having the benefit of this disclosure.

2. Ultrasound e.g., at about 0.1 MHz-40 MHz, and at a low acoustic pressure e.g., at about 20 kPa-6 MPa and a long cycle length (e.g., about >10 cycles) or a short cycle length (e.g., about <10 cycles) and high pulse repetition frequency (e.g., about >500 Hz) to produce radiation force and reduce the flow velocity of carriers. Again, the specific parameters chosen depend on the choice of carrier, as detailed further below, and can be readily determined by ordinarily skilled artisans having the benefit of this disclosure.

3. An ultrasonic pulse sequence of the above description followed by short pulses (e.g., about <10 cycles) of high acoustic pressure e.g., about 0.3 MPa to 20 MPa, which disrupts carriers, once they are concentrated by radiation force. As noted, the specific parameters chosen depend on the choice of carrier, as detailed further below, and can readily be determined by ordinarily skilled artisans having the benefit of this disclosure.

4. A combination of ultrasonic transducers, specifically designed for production of acoustic radiation force according to the description of 1 or 2 or 3, supra or any combination.

5. A single ultrasonic transducer, specifically designed for production of acoustic radiation force according to the description of 1 or 2 or 3, supra or any combination.

6. An ultrasonic system designed for simultaneous drug delivery with radiation force and imaging.

7. An ultrasonic system designed for simultaneous vasoporation and drug delivery with radiation force.

8. Any combination of the above techniques.

In preferred embodiments of the invention, a subject in need of diagnosis or treatment receives an injection of carriers, preferably loaded with a compound. Preferably the subject is mammalian, and more preferably is human. The compound preferably comprises a therapeutic agent such as, e.g., a drug, nucleic acid, or other therapeutic agent. An ultrasound transducer may be simultaneously, or immediately thereafter be positioned over the site of delivery such as, e.g., a tumor, or an inflamed joint, or a vascular lesion.

The pulse sequence of the ultrasound scanner produces bursts of radiation force to displace flowing carriers to the walls of blood vessels at the desired site. Interspersed with radiation force generating pulses, are high-acoustic pressure destructive pulses that rupture the carriers at the targeted site, releasing the drug at the targeted site.

The mechanical effects of ultrasound (with and without microbubbles) to alter the permeability of cells and vessels have now been well established. In addition, targeted drug delivery vehicles and acoustically-activatable vehicles have been developed and characterized, with a model developed to predict their behavior. An ultrasound system that implements these developments is provided by the present invention to realize the benefits of the methods of the invention.

In one aspect, the invention provides for a system to combine imaging and drug delivery. The system comprises the following components:

1. The system is capable of sweeping imaging frames through a three dimensional volume. Imaging frames should consist of typical clinical center frequencies (e.g., about 2-20 MHz), and typical acoustic pressures (e.g., mechanical index or MI<1.9).

2. In addition, the system interleaves imaging pulses with therapeutic pulses. These therapeutic pulses can take several forms:

a. For vehicles that contain gas as well as an oil or liquid, the use of a lower frequency pulse (e.g., with a center frequency of about 0.1 MHz-20 MHz) can be applied to fragment the vehicle. The advantage of this fragmentation is that particles small enough to easily extravasate from the vasculature are created, or alternatively the small particles may be pinocytosed. This process is repeated throughout the three dimensional region of interest. This process preferably is repeated each time the vasculature re-fills with the carrier. Usually, the time required for re-filling is on the order of about 5-20 seconds. The process preferably is repeated until the total volume of injected vehicles has been delivered to the desired site. This time can be determined using the imaging pulses described above.

b. For vehicles that include a targeting mechanism such as a ligand or predetermined charge distribution or are susceptible to radiation force, the therapeutic system has the ability to apply this force to bring the carrier ligand or charges into contact with the cells of interest. In order to accomplish this goal, either the imaging or therapeutic array transmits a sequence of low intensity (for example <800 kPa) long (for example, >10 cycles) pulse train to each area within the three dimensional volume. This radiation force sequence preferably is interleaved with imaging pulses, and preferably precedes the therapeutic pulses. The typical center frequency of operation for the therapeutic pulses will be on the order of from about 100 kHz to about 40 MHz, and more preferably from about 1 MHz-20 MHz.

c. To further deliver a drug to a region of interest, a therapeutic sequence that creates "vasoporation" is transmitted while microbubble-based or other compounds fill the vasculature. In this sequence, therapeutic pulses with a center frequency between about 0.1 MHz-5.0 MHz, and more preferably from about 0.75 MHz-1.5 MHz are applied to each region within the therapeutic volume at an intensity from about 0.1 MPa-10.0 MPa, and more preferably from about 0.75 MPa-2 MPa. These therapeutic pulses preferably are interleaved with the imaging pulses. Subsequent to or concurrently with the application of these vasoporation pulses, a drug that extravasates through this altered vasculature is administered, alone, or in association with a carrier.

The invention thus contemplates a system to carry out imaging along with therapeutic strategies described in a, b, or c either separately or in combination. The system provided by the present invention therefore includes the following aspects:

1. Transducer—a combined imaging and therapeutic transducer is provided. In one embodiment, the transducer uses an interface strategy such as is used for a 1.5 D array with the center array used for imaging and the outer arrays used for the therapeutic pulses. Such an arrangement is described in, e.g., U.S. Pat. No. 5,558,092, the entire disclosure of which is hereby incorporated by reference in its entirety. One implementation of this transducer 101 is diagrammed in FIG. 1 and comprises an inner imaging array 102 and an outer therapeutic array 103 for which the elements are expected, in preferred embodiments to be larger, and with a different spacing.

2. The transducer may be scanned mechanically to treat and or image the required three dimensional target site. Scanning may be accomplished manually, or automatically using computer guided robotics, as is well known to ordinarily skilled practitioners.

3. The ultrasound system timing is adjusted such that both imaging and therapeutic pulse sequences can be transmitted.

Further modifications to parameters such as, e.g., the duty cycle, pulse length, acoustic pressure, and center frequency may be altered by the practitioner or system depending on the flow rate of blood vessels at the desired site, the depth of the region of interest, and the specific properties of the carrier vehicle.

Compositions Useful for Practicing the Invention

Compositions comprising carriers and compounds are especially useful for practice of the present invention. In preferred embodiments, the carriers are acoustically active, and the compounds are therapeutically active. Such carriers and compounds are well known to those of skill in the art, and may be selected without undue experimentation by skilled practitioners having the benefit of this disclosure. Representative examples of useful compositions are described below.

Liquid and solid contrast agents containing entrapped gas are well known in the art and are useful for practice of the instant invention. See, e.g., U.S. Pat. Nos. 4,235,871; 4,265, 251; 4,442,843; 4,533,254; 4,572,203; 4,657,756; 4,681, 199; 5,088,499; 5,147,631; 5,228,446; 5,271,928; 5,380, 519; 5,413,774; 5,527,521; 5,531,980; 5,547,656; 5,558, 094; 5,573,751; 5,585,112; 5,620,689; 5,715,824; 5,769, 080; EP 0 122 624; EP 0 727 225; WO 96/40285; and WO 99/65467, the entire disclosures of which are hereby incorporated by reference in their entirety for all purposes. Microbubbles provided by these contrast agents act as sound wave reflectors due to the acoustic differences between the gas microbubble and surrounding liquid.

Compounds can be linked to or dissolved within carrier lipid coatings, or deposited in subsurface oil layers, or trapped within the carriers themselves.

U.S. Pat. No. 5,190,766 to Ishihara (incorporated herein by reference in its entirety for all purposes) teaches compositions and manufacturing techniques for selecting or producing and using a microcapsule or a particle containing a liquid/sol that has an acoustic impedance greatly different from the acoustic impedance of the ambience in which the drug is released and having acoustic characteristics such as the resonance frequency and the scattering/absorption characteristics that facilitate the use of the drug carrier in the ambience in which the drug is released. The patent describes methods and apparatus for loading an ultrasound contrast agent with a drug, administering the agent by injection into a vessel, imaging via ultrasound the accumulation of the injected agent, and promoting release of drug from the agent at a localized site through application of focused ultrasound energy at a frequency designed to induce resonance within the agent.

ALBUNEX® (Molecular Biosystems Inc., San Diego, Calif.) is another composition useful for practicing the instant invention. ALBUMIN is the generic name for ALBUNEX. ALBUNEX is an ultrasound contrast agent used in echocardiography and in other areas, it consists of microspheres of which more than 95% have a diameter in the range 1-10 microns. Methods to adsorb a compound of interest onto the protein coating of ALBUNEX are well known to ordinarily skilled practitioners.

Other carriers useful for practicing the invention include commercial sources of microbubbles and associated methods for loading drugs (hydrophobic or hydrophilic) exemplified by Optison (Molecular Biosystems), Imagent (Aliance Pharmaceuticals), DMP-115 (ImaRx Pharmaceutical), and BR1 (Brasco Imaging); as well as the acoustically active liposomes composed of small nongaseous multilamellar lipid vesicles (Alkan-Onyuksel, et al., *J. Pharm. Sci* 85:486-490 (1996) incorporated herein by reference in its entirety for all purposes), and acoustically active liposheres (ImaRx Therapeutics).

U.S. patent application Publication US 2002/0102215 A1 to Klaveness et al. (incorporated herein by reference in its entirety) discloses targetable diagnostic and/or therapeutically active agents comprising gas-filled microbubbles stabilized by monolayers of film-forming surfactants, optionally coupled or linked to a vector having affinity for a target site or structure within the body, and teaches incorporation of therapeutic compounds encapsulated in the interior of the microbubbles or attached to or incorporated in the stabilizing membranes.

Hollow polymeric contrast agents also are useful for practicing the invention and may be formed by microencapsulating a solid core of ammonium carbonate which is then removed by decomposition and freeze-drying. Suitable polymers preferably are FDA approved and susceptible to in vivo degradation such as, e.g., poly D,L(lactide-co-glycolide) (PLGA). Spray drying, coacervation and solvent extraction methods may be used. Ideally, the resulting particles have a mean particle size on the order of less than or equal to 10 μm. Compounds may be loaded onto the capsules by adsorption. Such methods are described in more detail in Wheatley, El-Sherif, et al., Mat. Res. Soc. Symp. Proc. Vol. 550:113-118 (1999), the entire disclosure of which is hereby incorporated by reference for all purposes.

Temperature activated gaseous precursor-filled microspheres useful for the practice of the invention are described in U.S. Patent Publication No. US 2003/0039613 A1 to Unger et al. Similar disclosures are found in U.S. Pat. No. 6,554,989 B1 to Unger et al., and in U.S. Pat. No. 6,416,740 B1 to Unger; formation of gas-filled lipid bilayers useful for practice of invention is described in U.S. Pat. No. 6,146,657 to Unger, et al. U.S. Pat. No. 5,770,222 to Unger et al. teaches therapeutic drug delivery systems comprising gas-filled microspheres comprising a therapeutic compound, along with methods for employing them in therapeutic drug delivery applications. U.S. Pat. No. 5,770,222 also teaches methods of and apparatus for preparing liposomes, including liposomes having encapsulated drugs, that are suitable for practice of the present invention. The entire disclosures of the publications and patents cited in this paragraph are hereby incorporated in their entirety for all purposes.

U.S. Patent Publication No. US 2003/0039613 A1 to Unger, et al. (incorporated herein by reference in its entirety for all purposes) also teaches procedures to adjust particle size, including extrusion, filtration, sonication, homogenization, employing a laminar stream of a core of liquid introduced into an immiscible sheath of liquid, extrusion under pressure through pores of defined size, and similar methods.

Particle sizes useful for practice of the present invention will vary depending on the makeup of a carrier. In general, particles on the order of 10 µm or less in diameter are preferred. Described below is a model that is useful for guiding the skilled practitioner on selecting frequencies, pressures, and other parameters, based on the size and physical properties of the carriers. Particle size may be determined using, e.g., a Model 770A Accusizer particle sizer (Particle Sizing Systems, Santa Barbara, Calif.). Especially useful for practice of the invention are particles that comprise an oil having a kinematic viscosity at 37° C. between about 1 $mm^2$/sec and about 100 $mm^2$/sec, or between about 10 $mm^2$/sec and about 80 $mm^2$/sec, or between about 20 $mm^2$/sec and 60 $mm^2$/sec. Kinematic viscosity can be measured using a device such as a KV5000 Kinematic Viscosity Bath available from Koehler Instrument Co., Inc. (Bohemia, N.Y.).

As described above, the present invention also may be practiced with carriers comprising targeting moieties designed to assist in the targeting of the carrier to a site. Such targeting moieties are well known in the art, and may be selected and incorporated into the carriers without undue experimentation by ordinarily skilled practitioners having the benefit of this disclosure. Exemplary teachings in the prior art relating to targeting moieties are provided below.

Methods suitable for coupling targeting moieties to carriers can be found in Hermanson, "Bioconjugate Techniques," Academic Press: New York, 1996; and in "Chemistry of Protein Conjugation and Cross-linking" by S. S. Wong, CRC Press, 1993, the entire disclosures of which are hereby incorporated by reference in their entirety for all purposes. Other suitable methods are taught in paragraphs 66 through 130 of U.S. Patent Application Publication U.S. 2002/0102215 A1 to Klaveness et al. Specific coupling methods include, but are not limited to, the use of bifunctional linkers, carbodiimide condensation, disulfide bond formation, and use of a specific binding pair, where one member of the pair is on the targeting agent and the other is on the carrier, e.g., a biotin-avidin interaction, see, e.g., Dayton et al. *J. Acoust. Soc. Am.* 112(5):2183-2192 (Nov. 2002), and references 10 through 14 cited in the bibliography (Dayton et al., and internal references 10 through 14 are hereby incorporated by reference in their entirety for all purposes).

The use of charged phospholipids are advantageous in that they contain functional groups such as carboxyl or amino that permit linking of targeting moieites, if desired, by way of linking units.

Suitable compositions for practicing embodiments of the invention using targeted carriers include those having an avidin biotin bridge to target an antigen as taught by Lindner and Kaul, *Echocardiography* 18(4):329-337 (2001). The initial step comprises administration of a biotinylated monoclonal antibody against the antigen followed by administration of avidin, and then administration of an emulsion of microbubbles containing a biotinylated phospholipid. Avidin forms a bridge between a surface expressing the antigen and biotinylated microbubbles.

MRX-408 manufactured by ImaRx Pharmaceutical Corp., Tucson, Ariz., USA is another suitable composition for practicing the invention. MRX-408 is a lipid-shelled microbubble having an oligopeptide sequence conjugated to microbubble surface which is recognized by the RGD-binding site of platelet IIB/IIIa receptors. The peptide is conjugated to the microbubble surface through a molecular spacer, polyethylene glycol, which allows a greater number of ligand-receptor pairs. See Lindner and Kaul, *Echocardiography* at 330.

Also suitable are microbubbles and acoustically active microemulsion agents that have been formulated with monoclonal antibodies that recognize ICAM-1 conjugated to their surface, such as those described by Lindner and Kaul, *Echocardiography* at 332, referencing internal refs. 19, 20, incorporated herein by reference in their entirety for all purposes. These formulations may include as therapeutic compounds, inhibitors of endothelial cell adhesion molecules such as ICAM-1 and proinflammatory cytokines for use in treating inflammatory disorders such as rheumatoid arthritis, and Crohn's disease. See Lindner and Kaul, *Echocardiography* at 333, and internal refs. 21, 23. Exemplary compounds comprise anti-ICAM-1; CD54 antibody—for rheumatoid arthritis); anti-TNF monoclonal antibody with methotrexate (also for rheumatoid arthritis); and chimeric monoclonal antibody cA2 to TNF for Crohn's disease.

Also suitable are immunoliposomes specific for tumors containing cytotoxic agents along with monoclonal antibodies against tumor-associated antigens conjugated to their surface such as described in Lindner and Kaul, *Echocardiography* at 333, and internal refs. 26, 27, the entire disclosures of which are hereby incorporated by reference in their entirety for all purposes. Specific examples include e.g., tumor antigen p185, encoded by the HER-2 protooncogene expressed on surface of certain breast, lung, and ovarian carcinomas. Immunoliposomes containing doxorubicin formulated with an Fab' against extracellular domain of p185 conjugated to surface are described in internal ref. 28 of Lindner & Kaul, *Echocardiography* (2001), the entire disclosure of which is hereby incorporated by reference in its entirety for all purposes.

Suitable targeting moieties and methods for their attachment to carriers also are listed in U.S. Patent Application Publication No. US 2002/0071843 A1 to Li et al., in, e.g., paragraphs 0109 through 0116, and in paragraphs 157 through 159, and in paragraphs 131-145 of U.S. Patent Application Publication U.S. 2002/0102215 to Klaveness, et al. the entire disclosures of which are incorporated by reference in their entirety for all purposes.

Other suitable targeting moieties include aptamers, and peptidomimetics.

Multivalent binding can be useful to enhance avidity and reduce "off-rates" so that binding persists long enough to permit imaging at convenient times after delivery of the agent. Polyvalent binding is possible with the use of more than one ligand type per carrier, or with mixtures of ligand-carrier constructs directed at different targets.

The invention may be practiced using a wide variety of different compounds, including therapeutic compounds having widely varying molecular weights, chemical composition, oil/water partition coefficient, etc. Exemplary compounds and carriers include bilayer-shelled microbubbles that contain concentrated drug between an inner and outer shell especially useful for packaging nonamphilic drugs into acoustically active microbubbles, as taught by Lindner &

Kaul, *Echocardiography* at 331. Also contemplated within the scope of useful compounds for practicing the invention are nucleic acids, including mRNA, cDNA, genomic DNA, antisense, and RNAi, any of which may further comprise semi-synthetic backbones or synthetic nucleic acids to modify stability or specificity.

Myocardial transfection in vivo by acoustic destruction of gene-laden microbubbles has recently been reported. See, e.g., Lindner, *Am. J. Cardiol.* 90(suppl):72J-80J (2002), and internal ref. 36; see also Lindner (2002) internal reference 40 showing oligonucleotides can bind to the surface of albumin-dextrose microbubbles, Lindner (2002) internal reference 41 showing microbubbles containing antisense oligonucleotides against c-myc proto-oncogene attenuating carotid neointimal hyperplasia post balloon catheter injury in pigs. Each of the reported compositions is useful for practice of the invention. Each of these references is hereby incorporated by reference in its entirety for all purposes.

Also useful in practicing the invention are stabilized gaseous microbubble contrast agents that have demonstrated potential for use as transfection agents by incorporating DNA directly into the bubble shell or interior, as described in Unger, et al. *Invest. Radiol.* 32:723-727 (1997); Shohet, et al. *Circulation* 101:2554-2556 (2000); reflective liposomes useful for specifically targeting endothelial integrins as described in Lanza, et al. *J. Am. Coll. Cardiol.* 19(3 Suppl A): 114A (1992); Demos, et al. *J. Am. Coll. Cardiol.* 33:867-875 (1999) and others described in Wickline and Lanza, *J. Cellular Biochemistry Supplement* 39:90-97 (2002), each of which is incorporated by reference in its entirety for all purposes.

Additional exemplary compounds are listed in U.S. Patent Publication No. 2003/0039613 A1 to Unger et al. (incorporated herein by reference in its entirety for all purposes) in, e.g., paragraphs 0156 through 0172 and include antineoplastic agents, hormones, anti-helmintics, antimalarials, and antituberculosis drugs; biologicals; viral vaccines; aminoglycosides; thyroid agents; cardiovascular products; glucagon; blood products; biological response modifiers; antifungal agents; vitamins; anti-allergic agents; circulatory drugs; metabolic potentiators; antivirals; anti-anginals; anticoagulants; antibiotics; antiinflammatories; antirheumatics; narcotics; opiates; cardiac glycosides; neuromuscular blockers; sedatives; local anesthetics; radioactive particles or ions; monoclonal antibodies; genetic material; and prodrugs.

Pharmaceutical Compositions of the Invention

Methods for treatment of various diseases are also encompassed by the present invention. Said methods of the invention include administering a therapeutically effective amount of a carrier and a compound, or, in alternate embodiments, of a compound without a carrier. The carriers and compounds useful for practicing the invention can be formulated in pharmaceutical compositions. These compositions can comprise, in addition to the compounds and optional carrier, a pharmaceutically acceptable excipient, bulking agent, buffer, stabiliser or other materials well known to those skilled in the art. Such materials should be non-toxic and should not interfere with the efficacy of the compound. The precise nature of the carrier or other material can depend on the route of administration, e.g. oral, intravenous, cutaneous or subcutaneous, nasal, intramuscular, intraperitoneal routes. In the practice of the invention, preferred administration routes include, e.g., intravascularly, intralymphatically, parenterally, subcutaneously, intramuscularly, intranasally, intrarectally, intraperitoneally, interstitially, into the airways, orally, topically, intratumorly. See, e.g., Unger, et al. U.S. Patent Publication No. US 2003/0039613 A1 at paragraph 0202.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody, nucleic acid, small molecule or other pharmaceutically useful compound according to the present invention that is to be given to a subject, administration is preferably in a "therapeutically effective amount" or "prophylactically effective amount" (as the case can be, although prophylaxis can be considered therapy), this being sufficient to show benefit to the subject. The actual amount administered, and rate and time-course of administration, will depend on the nature and severity of the condition being treated. Prescription of treatment, e.g. decisions on dose, timing, etc., is within the responsibility of general practitioners and other medical doctors, and typically takes account of the disorder to be treated, the condition of the subject, the site of delivery, the method of administration and other factors known to practitioners. Examples of the techniques and protocols mentioned above can be found in Remington's Pharmaceutical Sciences, 16th edition, Osol, A. (ed), 1980 (incorporated herein by reference for all purposes).

A composition can be administered alone or in combination with other treatments, either simultaneously or sequentially dependent upon the condition to be treated.

Radiation Sources and Parameters

The relationship between carrier translation, center frequency, pressure, pulse length and fundamental or harmonic resonance frequencies of insonified carriers are described in, e.g., Dayton, et al. *J. Acoust. Soc. Am.* 112 (5):2183-2192 (Nov. 2002) (incorporated herein by reference in its entirety for all purposes.) Further teachings about these relationships are set forth in the Examples below.

Ultrasound systems useful for practicing the invention include the phased system array (HDI c000cv, Advanced Technologies Laboratories) for delivering ultrasound and imaging, the system described in U.S. Pat. No. 5,558,092, to Unger, et al., and may include external application, preferred for skin and other superficial tissues, but for deep structures, application of sonic energy via interstitial probes or intravascular ultrasound catheters may be preferred.

The physics governing imaging, fragmentation, and steering (as by, e.g., radiation force) are well understood by ordinarily skilled practitioners having the benefit of this disclosure. For example, it is well known that harmonic emissions may be generated from insonated vesicles (usually at 2× frequency of incident therapeutic ultrasonic waves), and that such harmonic emissions are useful for, e.g., imaging. As described in U.S. Pat. No. 5,770,222 to Unger, et al., the microspheres useful for practicing the present invention have a peak resonant frequency of between about 0.5 MHz and about 10 MHz. Of course, the peak resonant frequency of gas-filled microspheres will vary depending on the diameter and, to some extent, the elasticity or flexibility of the microspheres, with the larger and more elastic or flexible microspheres having a lower resonant frequency than the smaller and less elastic or flexible microspheres.

The fragmentation or rupturing of microsphere carriers useful for practicing the invention is easily carried out by applying ultrasound of a certain frequency to the region of the subject where therapy is desired, after the carriers have been administered to or have otherwise reached that region. When ultrasound is applied at a frequency corresponding to the peak resonant frequency of the compound containing gas-filled microsphere carriers, the microspheres rupture and release their contents.

The peak resonant frequency can be determined by the ordinarily skilled practitioner either in vivo or in vitro, but preferably in vivo, by exposing the microsphere carriers to ultrasound, receiving the reflected resonant frequency signals and analyzing the spectrum of signals received to determine the peak, using conventional means. The peak, as so determined, corresponds to the peak resonant frequency (or second harmonic, as it is sometimes termed).

Gas-filled microsphere carriers will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and therapeutic release is improved, appreciable tissue heating does not generally occur (frequently no increase in temperature above about 2° C.), and less overall energy is required. Thus, application of ultrasound at the peak resonant frequency, while not required, is most preferred.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current edition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* 3rd Ed. (Plenum Press) Vols A and B(1992).

Introduction

Many promising studies indicate that ultrasound-enhanced drug delivery vehicles can be used to locally deliver a drug to a region of interest, with ultrasound imaging used to define the region to be treated and to monitor the inflow of the delivery vehicle. We have developed radiation force pulse sequences that first deflect a drug delivery vehicle to a vessel wall and then rupture the vehicle at that site. Drug delivery vehicles can be engineered to be manipulated by ultrasonic radiation force through the incorporation of a small volume of gas within a thick shell that contains the drug of interest. We refer to the engineered vehicles as acoustically-active liposheres (AALs) in that they have properties similar to ultrasound contrast agents, but have a thick shell that is on the order of 500 nm. In this case we consider an oil shell, although there are many other possibilities. Ultrasound contrast agents typically have a thin shell composed of lipid, albumin, or polymer. The inclusion of this small gas bubble within the AAL or contrast agent provides tremendous opportunities as the compressibility of air is 17,000 times greater than that of water, and the resulting acoustic impedance mismatch as compared with plasma provides the opportunity to detect or manipulate a single gas-filled vehicle in the body at clinical ultrasound pressures. Ultrasound is sensitive to a volume of such particles on the order of 0.01 pL. In addition, the vehicles can be designed such that ultrasound pressure produces fragmentation of a micron-sized sphere into particles on the order of tens to hundreds of nanometers, and these particles adhere to local endothelial cells. We explore the development of ultrasound techniques to locally concentrate a chemotherapeutic drug within the brain, crossing the blood-brain barrier ("BBB"). This is a unique problem and is critically important as the survival time with primary and metastatic brain tumors is low. Chemotherapy has been unsuccessful in general, and surgical debulking of the tumor and radiotherapy extend patient survival only by 6-12 months. New research studies have demonstrated that BBB permeability can be greatly increased for both hydrophilic and hydrophobic drugs through the application of systemic compounds that include bradykinin analogs and P-glycoprotein (P-gp) modulators. The disadvantage of the global increase in BBB permeability produced by these compounds is that the simultaneous application of chemotherapy at the desired concentrations can result in a severe neurotoxicity. The present invention addresses this problem since the drug is concentrated on the luminal surface of the endothelial cells in the desired region, and this increased concentration, especially when combined with, e.g., P-gp modulation will lead locally to increased drug concentration in the tumor and brain-surrounding tumor region. Thus, ultimately, by combining increased BBB permeability with local delivery of a chemotherapeutic to endothelial cells in a region of interest, the methods of the present invention significantly increase the effectiveness of chemotherapy in brain tumors. The examples below are designed to illustrate ultrasound-enhanced local drug delivery of a hydrophobic drug to the brain.

A model for the oscillation of these agents has been developed. Also, our research on the physical and acoustical dynamics of acoustically active liposomes ("AALs") has shown that specific acoustic parameters are required to produce the desired response by these agents. We have demonstrated that radiation force, which acts on particles in an acoustic field, has the unique ability to manipulate and concentrate contrast agents and AALs along the wall of a vessel. Particles localized along the vessel wall travel at a reduced velocity, further increasing the capture efficiency of these vehicles by endothelial cells. A drug delivery vehicle, i.e., a carrier, containing a gas core can be deflected to a vessel wall, and then can be fragmented producing very small local fragments. These submicron fragments may be taken up by endothelial cells or extravasate into the extracellular fluid space. In particular, paclitaxel released by these vehicles can cross the lipid phase of the membrane into the endothelial cells.

In Example 1 we develop and evaluate a model for the displacement produced by ultrasonic radiation forces applied to AALs. In Example 2, acoustically-mediated transfer of fluorescently-labeled paclitaxel to endothelial cells is assessed. In Example 3, the ability of AALs containing F18-labelled paclitaxel to concentrate the drug within the brain with and without co-administration of a P-glycoprotein blocker is determined.

Background and Significance

Local Drug Delivery to the Brain

With the development of new biologically-active therapeutics, many of which are effective at nanomolar concentrations, there is a tremendous opportunity for improvement in therapeutic efficacy as compared with current cancer therapies. In addition, there is great potential for ultrasound-enhanced drug delivery. One great advantage of this approach is that imaging can be coincident with therapy. For purposes of illustration, we develop drug delivery strategies for the unique setting of drug delivery to the brain; however, the techniques of the present invention have application in many areas, including cardiology, inflammation, and peripheral vascular disease.

The problem of drug delivery to the brain has some unique aspects due to the tight endothelial cell junctions and multi-drug resistant properties of the BBB. Many approaches have been considered to increase BBB permeability to drugs and several classes of drugs have been considered for delivery. Drugs such as the lipophilic paclitaxel and the hydrophilic carboplatin had not achieved sufficient concentrations within gliomas to produce an effective response. Recently, CEREPORT (RMP-7), generic name CARBOPLATIN, was developed as a pharmaceutical analog of bradykinin, with a substantially longer half life. RT Bartus, et al. *J. Pharmacol. Exp. Ther.:* 293(3):903-11 (June 2000)(incorporated herein by reference in its entirety for all purposes).

Following the administration of Cereport, it has been shown that carboplatin reaches much higher intra-tumoral and brain concentrations than without Cereport. D F Emerich, et al. *Clin. Pharmacokinet.* 40(2):105-23 (2001)(incorporated herein by reference in its entirety for all purposes). Some regions demonstrate a several fold increase in uptake. The mechanism for this change is assumed to be the effect of Cereport on the tight junctions of the BBB. Interestingly, however, Cereport does not increase the uptake of the lipophilic drug paclitaxel. This lipophilic drug diffuses into the brain through the lipid phase of the endothelial cell membranes. Bartus, et al. 2000.

Paclitaxel does not typically achieve high concentrations within the brain or tumors in large part because it is rapidly transported back into the blood by the P-glycoprotein ("P-gp") system. P-glycoprotein is a 170,000 dalton membrane protein that functions as a drug efflux pump, and its overexpression is one of the most consistent alterations in the multi-drug resistance phenotype. It has been demonstrated in P-glycoprotein knockout mice that the penetration of paclitaxel into the brain is markedly increased. Numerous agents have been studied in an effort to overcome P-gp mediated multi-drug resistance, including tamoxifen, Valspodar (PSC 833), verapamil, cyclosporine A, and VX-710.

Valspodar is a particularly interesting compound, as it sensitizes cancer cells to chemotherapy through the potentiation of ceramide formation. As ceramide is a second messenger in chemotherapy-induced apoptosis, Valspodar is a particularly attractive target for therapeutic co-administration. Whereas paclitaxel alone did not affect tumor volume, co-administration of paclitaxel (intravenous) and Valspodar (given peroral) reduced tumor volume by 90%. In this study, we use ultrasound-enhanced drug delivery to produce locally increased concentrations of paclitaxel, and evaluate its ability to cross the BBB with and without a P-gp modulator. This greatly increased local concentration further increases efficacy, and reduces systemic toxicity. The methods of the invention are superior to convection-enhanced delivery due to the elimination of the requirement for inter-cerebral administration.

Both endothelial-based and epithelial-based receptors are attractive for local delivery with AALs. Since many new and particularly anti-angiogenic therapies primarily act on endothelial cells, effective strategies do not require drug delivery vehicles that extravasate.

Substantial differences in drug concentrations have also been shown between primary and metastatic tumors, with primary tumors shown to exhibit lower concentrations of systemic drugs. The methods of the present invention address the extraordinarily difficult problem of drug delivery to primary brain tumors.

In-vitro models of the BBB: A cell culture model used in this study has proven to be of great value in many studies of the blood-brain barrier and associated drug transport (see, e.g., R D Hurst, et al., *J. Cell. Physiol.* 167(1):81-88 (April 1996); K Takahashi, et al., *In Vitro Cell Dev Biol.* 26(3 Pt 1):265-274 (March 1990); R C Janzer and M C Raff *Nature* 325(6101):253-27 (Jan. 15-21 1987) January 15-21; and G A Grant, et al., *News Physiol Sci.* 13:287-293 (December 1998) (each of which is hereby incorporated by reference in its entirety for all purposes). The ECV304 phenotype develops a raised transendothelial electrical resistance when co-cultured with rat c6 glial cells. This is a static system in which endothelial cells are cultured on permeable inserts, and their proximity to the glial cells induces a tight barrier, with many of the features of the in vivo blood brain barrier. This combination has also been shown to yield overexpression of P-glycoprotein.

Local delivery: Local drug delivery has been considered for many years in order to reduce the toxic effects of some compounds on the surrounding tissue, with methods including long-circulating liposomes, heat-activated liposomes, macromolecular carrier systems, and the AALs considered here (see, e.g., T. Lian, R. J. Y. Ho, *Journal of Pharmaceutical Sciences,* 90 (6):667-680 (June 2001); T. M. Allen, C. B. Hansen, D. E. Lopes de Menezes, *Advanced Drug Delivery Reviews,* 16:267-284 (1995); Y. Takakura, M. Hashida, *Pharmaceutical Research,* 13 (6):820-831 (1996); and E C Unger, et al. *Invest Radiol.* 33(12):886-892 (December 1998) (each of which is incorporated herein by reference in its entirety for all purposes). New strategies are now coming to fruition with commercially available systems employing liposomes, polyethyleneglycol (PEG)-coated liposomes, transdermal delivery systems, and transdermal systems with "electrotransport technology." Successful targeted delivery vehicles have also recently been reported. There are now approved and highly successful examples of antibody (Rituximab), radiolabeled antibody (Yttrium-90 ibritumomab tiuxetan), and peptide-targeted therapies (In-111 DTPA, "Octreotide"). Such strategies now produce a response in more than 50-70% of patients with non- Hodgkin's lymphoma, with complete remission in more than 30%. Clearly, targeting approaches can be successful; however, these compounds must still cross the BBB in order to be effective in the treatment of brain tumors. In the following examples, we address the problem of crossing the BBB.

Local drug delivery to tumors has been considered for many years with a goal of reducing the toxic effects of some compounds on the surrounding tissue, using methods that include long-circulating liposomes, heat-activated liposomes, and macromolecular carrier systems. The particle size is particularly critical, with liposomes smaller than 200 nm being most effective, and a negative surface charge is also important. In general, liposomes have demonstrated an ability to attenuate toxicities by their different pharmacokinetic profiles and patterns of distribution. Liposome encapsulation of doxorubicin has been shown to reduce cardiac toxicity. Paclitaxel can be suspended within oil and locally and effectively delivered. Preliminary data suggest that encapsulation of paclitaxel in a liposome or AAL can greatly decrease neurotoxicity eliminating the need for Cremophor. A breakthrough in increasing the longevity of liposome circulation has been PEG coating of the liposome. Again, however, these schemes have not been effective in increasing the concentration of drug within the brain.

Our approach is substantially different than HIFU (high intensity focused ultrasound) approaches that rely upon high ultrasound pressure or increases in temperature to destroy tissue, and approaches that rely solely upon changes in the permeability of the cell membrane. Typical ultrasound modes of operation are summarized in Table 1. One objective of the present invention is to locally deliver new therapeutics to the brain using radiation force and fragmentation modes, with associated the low ultrasonic pressure. This approach avoids difficulties in obtaining high ultrasound intensities in the brain with associated diffuse toxicity. Given that many new drugs are active at nanomolar concentrations, the local delivery of very small quantities of drugs is expected to have a great impact. Many groups have investigated the change in cell membrane permeability produced by the oscillation of an ultrasound contrast agent. In M Ward, J Wu, J F Chiu, *Ultrasound Med Biol* 26(7):1169-1175 (September 2000) (incorporated herein by reference in its entirety for all purposes), it was shown that the contrast agent must be located within a few microns of the cell in order to change the cell membrane permeability, and therefore a large volume of the contrast agent may be needed to cause a clinically significant response. A proportion of cells that have been very close to a bubble with sufficient wall velocity to affect the membrane will also die, and only a small number of endothelial cells demonstrate a change in permeability at reasonable concentrations. In the examples below, we concentrate on ultrasound-triggered drug delivery to provide chemotherapy to many endothelial cells within a region of interest, with the advantage that the cell is not required to be immediately adjacent to the AAL to be treated.

TABLE 1

| Modes | Center Freq. | Pressure | Mechanical Index |
|---|---|---|---|
| Radiation force | optimal at resonance 2.5-5 MHz | 50-200 kPa | 0.02-0.12 |
| AAL Fragmentation | 1-1.5 MHz | 1.6 Mpa | 1.3-1.6 |

TABLE 1-continued

| Modes | Center Freq. | Pressure | Mechanical Index |
|---|---|---|---|
| Typical Imaging | 1.7-10 MHz | up to 6 MPa | <1.9 |
| HIFU | 100 kHz-3 MHz | up to 20,000 Watts/cm$^2$ (typically > 6 MPa) | |

PET imaging of biodistribution and multidrug resistance: Eckelman and collaborators have demonstrated that a set of radiolabelled paclitaxel compounds can be used to assess the biodistribution of paclitaxel and multidrug resistant tumors. F18-fluoropaclitaxel shows high uptake in many tissues and rapid clearance. F18-fluoropaclitaxel uptake in the brain of P-gp knockout mice is increased 1400% relative to wildtype controls. Preadministration of XR9576, a P-gp modulator increased the uptake of F18-fluoropaclitaxel by 20%; however, this increase was not significant. In the example below, we use Valspodar as the P-gp modulator, as it has been shown to significantly increase brain concentrations of paclitaxel when co-administered.

Contrast Agents and AALs

The effect of ultrasound on contrast agents and AALs is best determined by optically measuring the radial oscillations (radius-time curve) of the insonified agent. During an acoustic pulse, a highly compressible agent expands and compresses with the applied pressure rarefaction and compression. This oscillatory response generates a distinct echo that can be detected with a clinical imaging system. From the radius-time curve, the probability of destruction and magnitude of radiation force can be estimated. Parameters such as acoustic pressure, center frequency, and pulse length can be optimized. In addition, the acoustic signature can be directly measured with an ultrasonic transmission and reception system and used in conjunction with optically-acquired radius-time curves.

We have employed a 100 million frame per second optical system that has provided the first opportunity to image agent dynamics during insonation. As a result, we are able to tease apart phenomena that affect the scattered echoes. The effects of radiation forces and the behavior of phagocytosed and sub-micron contrast agents have also been characterized. In the examples below, these methods are applied to the evaluation of new drug delivery vehicles.

In addition, we have elucidated the mechanisms of contrast agent and AAL destruction and the parameters that produce these destruction mechanisms. The mechanisms of destruction include fragmentation of the bubble into smaller bubbles and/or diffusion of the encapsulated gas, however fragmentation is desired for local drug delivery. Within the modalities used in medical imaging, the ability to specifically destroy a particle in a region is unique to ultrasound.

In the examples, we describe a scheme to locally deliver drugs to the brain using ultrasound-activated drug delivery vehicles that contain a gas core. We employ a high-speed imaging and streak camera (100 million frames per second) that can determine the fragmentation mechanisms. A new carrier has been created using triacetin, a low-viscosity oil, which produces an AAL that is far superior to previous AALs (with corn or soybean oil). A far lower pressure can deflect and disperse triacetin AALs as compared with soybean AALs. The oil is dispersed with insonation, and the diameter of the resulting droplets can be in the tens to hundreds of nanometers (small enough to penetrate through the vessel wall), if the proper ultrasound parameters are chosen.

The behavior of these carriers during insonation and the potential for AAL destruction can be considered both from the view of previous investigations of bubble dynamics, and from prior work on liquid droplets within an acoustic standing wave. Relative expansion of a microbubble is defined as the maximum radius, $R_{max}$, divided by the resting radius, $R_o$, and has been correlated with the cavitation threshold and with fragmentation. M. S. Plesset, T. P. Mitchell, *Quart. Appl. Math.*, 13:419-430 (1956) (incorporated herein by reference in its entirety for all purposes). Relative expansion thresholds for cavitation range from 2.32 to 3.46 (R. E. Apfel, C. Holland, *Ultrasound in Medicine and Biology*, 17 (2):179-185 (1991) (incorporated by reference in its entirety for all purposes)). A related criterion, based on shape stability analysis, was derived by Plesset and Mitchell, who predict that when the minimum microbubble radius decreases below one tenth of the maximum radius that occurs during peak expansion, the microbubble will become violently unstable and fragment. Apfel et al., supra, show that a decreased center frequency reduces the threshold pressure required for cavitation and increases the resting radius for which the bubble can be fragmented. Non-spherical shape oscillations and instabilities of bubbles are often precursors for destruction. We have also demonstrated the effect of non-spherical oscillations on AAL breakup (J. Allen, D. May and K W Ferrara, *Ultrasound in Medicine and Biology*, Vol. 28(6):805-816 (July 2002) (incorporated herein by reference in its entirety for all purposes). One example of such previous work is the investigation of the levitation of millimeter size liquid drops in an acoustic standing wave (C. P. Lee, A. V. Anikumar, T. G. Wang, *Physics of Fluids*, 6(11):3554-3566 (1994) (incorporated herein by reference in its entirety for all purposes)). This work demonstrated the presence of capillary waves and turbulence on the shell surfaces. If the entire drop does not fragment, satellite drops may still be emitted. Optical observations have previously shown that fragmentation of contrast agents and AALs is possible at clinical pressures (D. May, J. Allen, and K. W. Ferrara, *IEEE Transactions on UFFC*, 49(10):1400-1410(October 2002) (incorporated herein by reference in its entirety for all purposes)).

Radiation force: The effects of radiation force were first reported in 1906 by C. A. Bjerknes and his son V. F. K. Bjerknes, when they observed the attraction and repulsion of air bubbles in a sound field. Over the next fifty years, several research groups published theoretical analyses of radiation force on spheres. Acoustic radiation forces on bubbles, or "Bjerknes forces" as they are sometimes still referred to, were not experimentally studied until almost 1970. In 1969, Eller and Crum examined the effects of radiation forces on bubbles in a cylindrical vessel energized by an acoustic transducer. Macedo and Yang studied the effects of radiation force generated by an acoustic transducer on air bubbles in a flow stream. In 1975, Crum published further analysis of Bjerknes forces after studying the forces produced by pressure waves acting upon bubbles within a vibrating vessel. In each of these cases, the air bubbles studied were on the order of tens of microns in radius, and the acoustic frequency was on the order of tens of kHz. Although this research involved radiation forces interacting with bubbles, it did not consider a parameter range (bubble size, acoustic frequency) relevant for clinical applications. Clinical ultrasound frequencies are on the order of MHz, and microbubbles are on the order of microns in diameter. In addition, clinical ultrasound typically involves traveling waves, rather than standing waves, which were studied in previous experiments. The first experimental analysis of radiation force on micron-sized bubbles was reported by one of the present inventors and collaborators (see, e.g., P. Dayton, K. Morgan, S. A. Klibanov, G. Brandenburger, K. Nightingale and K. Ferrara, *IEEE Transactions on Ultrasonics, Ferroelectrics, and Frequency Control*, 44(6): 1264-1277 (1997); P. Dayton, "The effects of acoustic radiation force on contrast agents: experimental and theoretical analysis," Ph.D. Dissertation, University of Virginia, August 2001; Paul A. Dayton, John S. Allen, Kathy W. Ferrara, *Journal of the Acoustical Society of America*, 112(5):2183-2192 (Nov. 2002); and P. Dayton, A Klibanov, G. Brandenburger, K. Ferrara, *Ultrasound and Medicine and Biology*, 25(8):1195-1201 (1999) (the entire disclosures of which are hereby incorporated by reference in their entirety)). Many other researchers have since published analyses of radiation force on microbubbles from a theoretical point of view. Also, local drug delivery of AALs can be facilitated using primary radiation forces by reducing the velocity of microbubble transit as well as displacing bubbles to the vessel walls (P. Dayton, A Klibanov, et al., (1999)).

Figure 2:
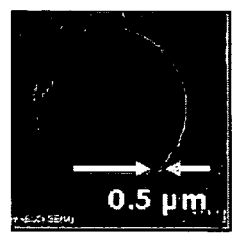
FIG. 2 is an electron micrograph of an acoustically active liposome.

Our examples are designed to validate models to predict the oscillation of AALs, to predict the translation of contrast agents and AALs, and to demonstrate the potential to transfer dye and drugs to surrounding cells. The behavior of AALs has been well-characterized in vitro, and they have been used to disseminate a dye and paclitaxel in vivo. Radiation force manipulation of contrast agents (in vitro and in vivo), and AALs (in vitro) has been demonstrated. Transverse cryo-electron microscopy of an AAL is shown in FIG. 2. The oil shell has a thickness of approximately 500 nm, for an agent with a diameter of approximately 8 microns.

Example 1

Oscillation of Contrast Agents and AALs Leading to Fragmentation and Radiation Forces To improve the local delivery of a drug, it is important to deliver the agent to the vessel wall, to fragment the delivery vehicle into sub-micron particles, and separate the oil and drug components, if possible. The oscillation and fragmentation of the AALs are highly dependent on the viscosity of the oil, with triacetin observed to be particularly effective for acoustic excitation and fragmentation. Our results indicate that the number and size of fragments, as well as the mechanism of microbubble destruction, are dependent on the ultrasonic parameters (see, e.g., D. May, J. Allen, and K. W. Ferrara, (October 2002) (incorporated herein by reference in its entirety for all purposes)). In this example, we first review our models for the oscillation of contrast agents and AALs, as the solution of equations (1)-(3) is used to predict the time-dependent volume of the agent, and thus the radiation force in equation (11). Also, fragmentation occurs when the expansion of the agent reaches three times the resting radius. We have created and validated a model for the oscillation of a contrast agent over time (K. Morgan, J. Allen, P. Dayton, J. Chomas, A. Klibanov, K. Ferrara, *IEEE Trans. On Ultrasonics, Ferrelectrics and Frequency Control*, 47(6):1494-1509 (2000) (incorporated herein by reference in its entirety for all purposes)), and the resulting equation is Eq. 1.

$$\rho R \ddot{R} + \frac{3}{2}\rho \dot{R}^2 = \left(P_0 + \frac{2\sigma}{R_0} + \frac{2\chi}{R_0}\right)\left(\frac{R_0 - h^3}{R^3(t) - h^3}\right)^\gamma \left(1 - \frac{3\gamma}{c}\dot{R}\right) - \quad (1)$$

$$\frac{4\mu\dot{R}}{R} - \frac{2\sigma}{R}\left(1 - \frac{1}{c}\dot{R}\right) - \frac{2\chi}{R}\left(\frac{R_0}{R}\right)^2\left(1 - \frac{3}{c}\dot{R}\right) -$$

$$12\mu_{sh}\varepsilon \frac{\dot{R}}{R(R-\varepsilon)} - (P_0 - P_{driv}(t))$$

where the time-dependent radius, wall velocity and wall acceleration are given by $R$, $\dot{R}$ and $\ddot{R}$, respectively. The hydrostatic pressure is $P_0$, and the acoustical forcing pressure is $P_{driv}(t)$. The known parameters are liquid density, $\rho$, liquid viscosity, $\mu$, the polytropic gas exponent, $\gamma$, surface tension, $\sigma$, and the speed of sound, $c$. The parameters that were estimated for the shell properties are the shell elasticity modulus, $\chi$, and the product of shell thickness, $\epsilon$, times the shell viscosity, $\mu_{sh}$. Predicted echoes at a distance r from the bubble, P(r), can be generated from the radius, velocity and acceleration of a bubble by the relationship:

$$P(r) = -\rho\dot{\Phi} = \frac{\rho}{r}(R^2\ddot{R} + R\dot{R}^2) \quad (2)$$

where $\Phi$ is the velocity potential. This model has been validated over a wide range of microbubble sizes and imaging parameters (D. Patel, P. Dayton, J. et al., Submitted to *IEEE Transactions on Ultrasonics, Ferroelectrics, and Frequency Control*; R T Bartus, P Snodgrass, et al., *J Pharmacol Exp Ther.* 293(3):903-11 (June 2000) (the entire disclosures of which are incorporated by reference in their entirety for all purposes)). Based on these equations, the radial oscillations, acoustic echo, and spectrum have been predicted for a range of transmitted conditions.

A preliminary model for the oscillations of a thick-shelled drug delivery vehicle has been developed and a preliminary evaluation of the performance of drug delivery vehicles has been performed (D. May, J. Allen, and K. W. Ferrara, *IEEE Transactions on UFFC*, 49(10):1400-1410 (October 2002); J. Allen, D. May and K W Ferrara, *Ultrasound in Medicine and Biology*, 28(6):805-816 (July 2002) (the entire disclosures of which are incorporated by reference in their entirety for all purposes)). The time-dependent equation for the driven vehicle is given by (3).

$$R_1\ddot{R}_1\left[1 + \left(\frac{\rho_2 - \rho_1}{\rho_1}\right)\frac{R_1}{R_2}\right] + \dot{R}_1^2\left[\frac{3}{2} + \left(\frac{\rho_2 - \rho_1}{\rho_1}\right)\frac{4R_2^3 - R_1^3}{2R_2^3}\frac{R_1}{R_2}\right] = \quad (3)$$

$$\frac{1}{\rho_1}\left[p_{go}\left(\frac{R_{10}}{R_1}\right)^{3\kappa} - P_\infty(t) - \frac{2\sigma_1}{R_1} - \frac{2\sigma_2}{R_2} + -4\mu_s\dot{R}_1\left[\frac{R_2^3 - R_1^3}{R_2^3 R_1}\right]\right] +$$

$$4\mu_l\frac{R_1^2\dot{R}_1}{R_2^3}\Bigg].$$

where we define the following notation: $\dot{R}$, wall velocity, $\ddot{R}$ wall acceleration, $R_1$ radius of gas core, $R_2$, radius of outer liquid shell, $R_1$ inner radius of, $R_2$, outer radius, $R_{10}$, equilibrium inner radius, $R_{20}$, equilibrium outer radius, $\rho_2$, density of the shell, $\rho_1$, density of the liquid, $\sigma_1$, surface tension at the inner radius, $\sigma_2$, surface tension at the outer radius, $\kappa$, polytropic gas exponent, $\mu_s$, shear viscosity of the shell, $\mu_1$, shear viscosity of the liquid, p, pressure, $P_\infty$, pressure at infinity, $p_{go}$, initial gas pressure (with respect to inner radius). Any acoustic forcing enters in the pressure at infinity.

The inner and outer radius are related by equation 4.

$$R_1 = (R_2^3 + R_{10}^3 - R_{20}^3)^{1/3} \quad (4)$$

Optical observations of radial oscillations: Our experimental system combines an optical system and an acoustical system in order to observe the radial fluctuations of an agent during insonation. The optical system is comprised of an inverted microscope (Olympus IX70, Melville, N.Y.) with a 100× objective (Zeiss Achroplan 100×, NA=1.0, Carl Zeiss, Inc., Thornwood, N.Y.). The images are captured with a high-speed digital camera capable of 100 million frames per second (Imacon 468, DRS Hadland, Inc., Cupertino, Calif.). A xenon strobe provides illumination of the microbubbles. This light is transferred to the imaging area by a fiber optic cable. Timing of the camera shutter, strobe, and waveform generator is controlled directly by a dedicated computer. The camera generates seven images of a bubble with variable shutter duration (10 ns-1 ms) and time delay from insonation. An eighth image displays one optical vertical line-of-sight over time. When the vertical line is positioned over the center of the bubble, this "streak" image represents the diameter of the bubble as a function of time (an M-mode image of a line through the center of the bubble over time). The temporal resolution of the streak image is approximately 10 ns and the spatial resolution is 0.12 μm/pixel. The streak image is converted to a radius-time curve in Matlab by measuring the diameter at each time using a threshold criterion. The streak image is shown in gray scale, and the left hand side of the image can be used to estimate the resting microbubble diameter, as it precedes insonation.

Figure 3:
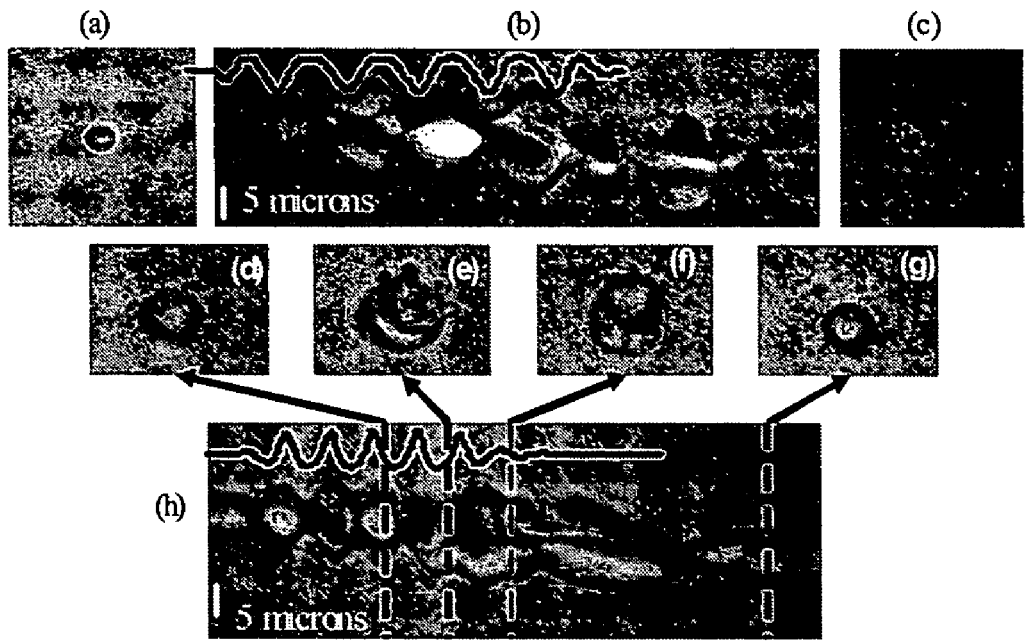
FIG. 3 shows 2D and streak images for two AALs during destruction.

FIG. 3 shows the streak and 2D images for two cases in which an AAL is destroyed, one small AAL in FIGS. 3a-c and a second larger AAL in FIGS. 3d-h. Note the small resting diameter in FIG. 3a (approximately 2 microns). The diameter changes over time in the streak image (FIG. 3b). The final set of fragments includes a small set of particles in FIG. 3c. This destruction mode, in which the AAL collapses symmetrically, is observed for small agents. For an AAL with a resting diameter greater than the resonant size at the transmitted center frequency, surface oscillations are often observed in the 2D images with protrusions visible in FIG. 3e and FIG. 3f. A set of small fragments is produced, although one large fragment is also visible in FIG. 3g. Thus, for the AAL, the observed destruction mechanism varies with the resting radius, with AALs near resonance size undergoing a symmetric collapse and producing a set of small fragments. Resonant size depends on the transmission frequency, but will include diameters between 3-6 microns. During the insonation of a larger AAL with a resting radius between resonance size and twice resonance size, surface waves become visible and the oscillation is frequently asymmetric. For a resting radius of approximately twice the resonance size, the destruction mechanism changes to a pinch-off, with one fragment containing a large fraction of the original volume.

A series of experiments has been conducted to determine the maximum expansion and probability of fragmentation for a range of vehicle diameters, center frequencies, and pulse lengths. The results of these experiments have been compared with the predictions from eqs (3)-(4) briefly summarized below and in D. May, J. Allen, and K. W. Ferrara, *IEEE Transactions on UFFC*, 49(10):1400-1410 (October 2002); J. Allen, D. May and K W Ferrara, *Ultrasound in Medicine and Biology*, 28(6):805-816 (July 2002)

Figure 4:
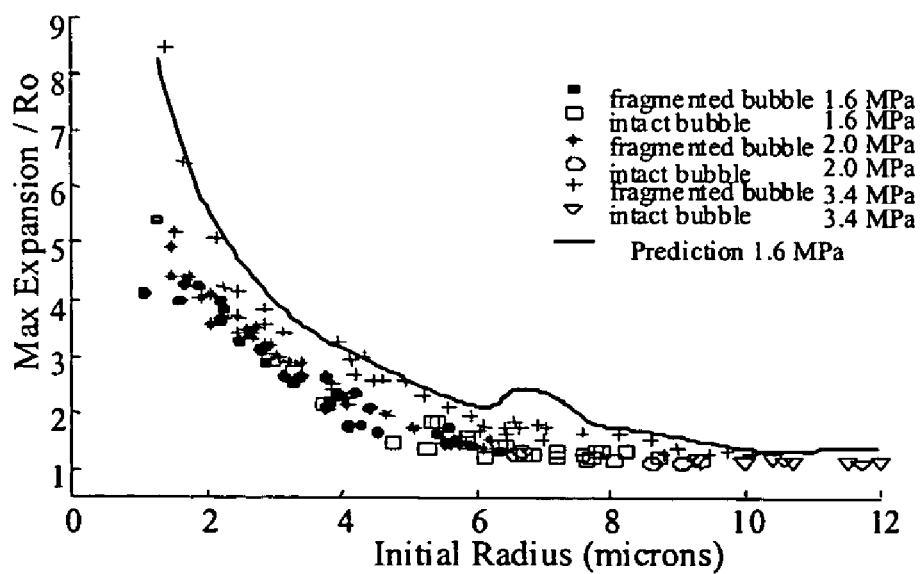
FIG. 4 is a summary graph of the maximum expansion for a range of AAL initial diameters for a transmitted center frequency of 1.5 MHz and a pulse length of 5 cycles.

(the entire disclosures of which are hereby incorporated by reference in their entirety for all purposes). FIG. 4 provides a summary of the maximum expansion for a range of AAL initial diameters for a transmitted center frequency of 1.5 MHz and a pulse length of 5 cycles. Note that the maximum expansion varies according to the initial radius, with expansion ratios greater than 2 frequently resulting in fragmentation. The maximum expansion of the AAL depends on the transmission center frequency, with a higher frequency resulting in a smaller expansion and a shift in the threshold radius for fragmentation. For equivalent imaging parameters, the maximum expansion of the AAL within the first cycle is similar to that of a lipid-shelled contrast agent, and subharmonics appear for the contrast agent and AAL for a similar radius and frequency. Thus, in some aspects the delivery vehicle functions in a similar manner to a contrast agent.

Figure 5:
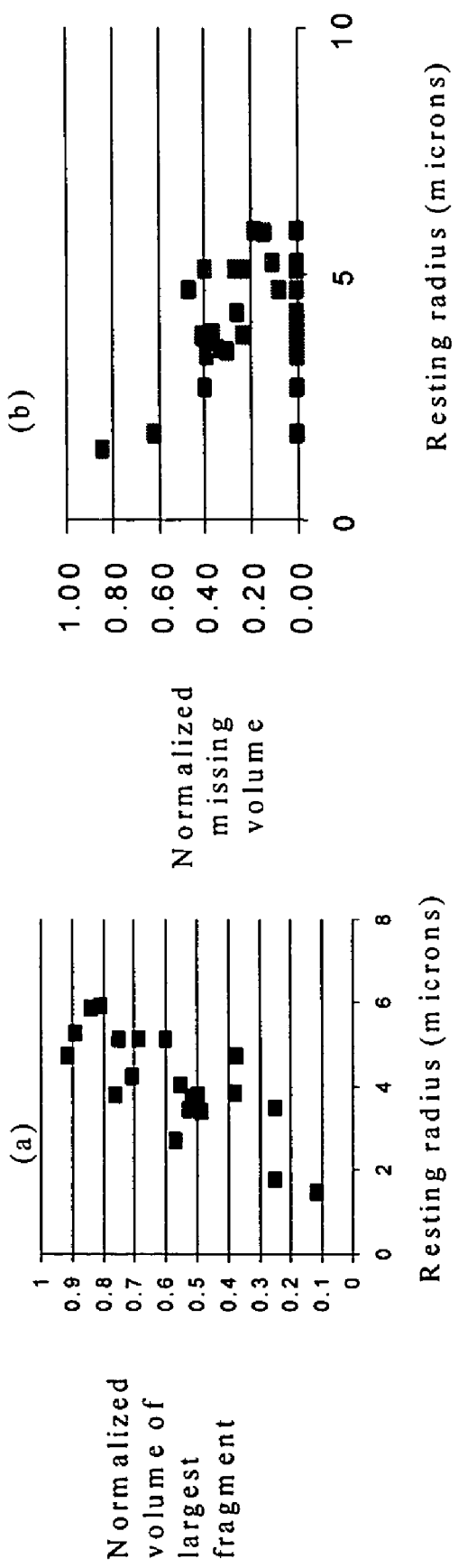
FIG. 5*a* is a graph that provides the normalized volume of the largest fragment and FIG. 5*b* is a graph that provides the volume of fragments that are smaller than the system optical resolution (0.1 micron) or have traveled beyond the optical focus and are no longer visible.
Figure 6:
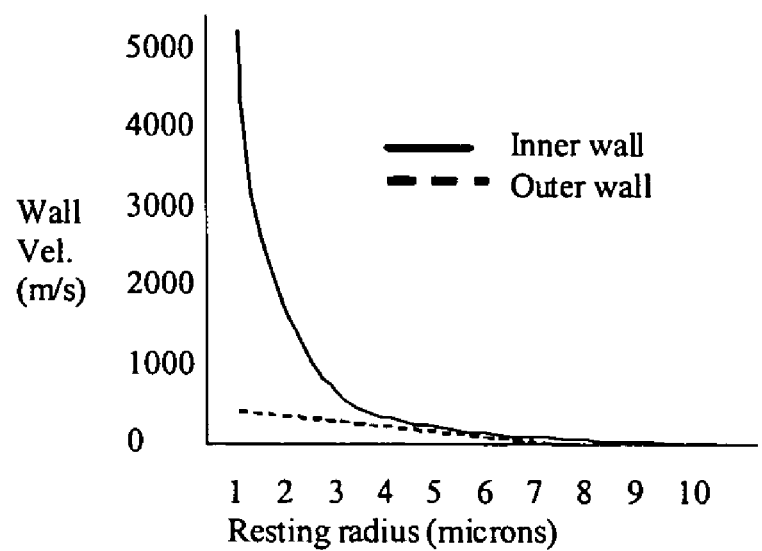
FIG. 6 is a graph illustrating predicted inner and outer wall velocity.

FIG. 5a provides the normalized volume of the largest fragment and FIG. 5b provides the volume of fragments that are smaller than our optical resolution (0.1 micron) or have traveled beyond the optical focus and are no longer visible. For a small resting radius and frequency of 1.5 MHz, the fractional volume in each fragment is quite small and more than 50% of the original volume cannot be visualized. In order to better understand the mechanisms behind the destruction of the AAL, we also examine the predicted inner and outer wall velocity (based on (3) and (4)) in FIG. 6. This figure demonstrates that for a small resting radius, tremendous differences exist between the radial velocity of the inner and outer wall of the oil layer, and this difference leads to destruction.

Example 2

In vivo Studies with AALs

Figure 7:
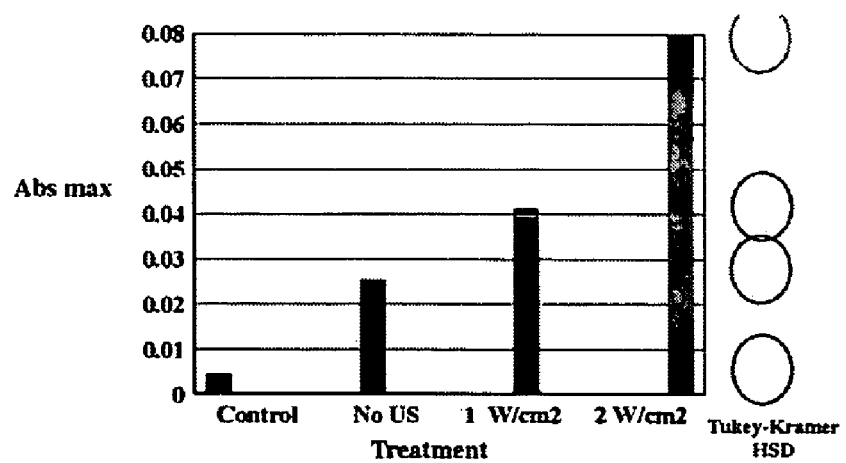
FIG. 7 is a graph illustrating ultrasound delivery in mice using Sudan Black as a model drug.
Figure 8:
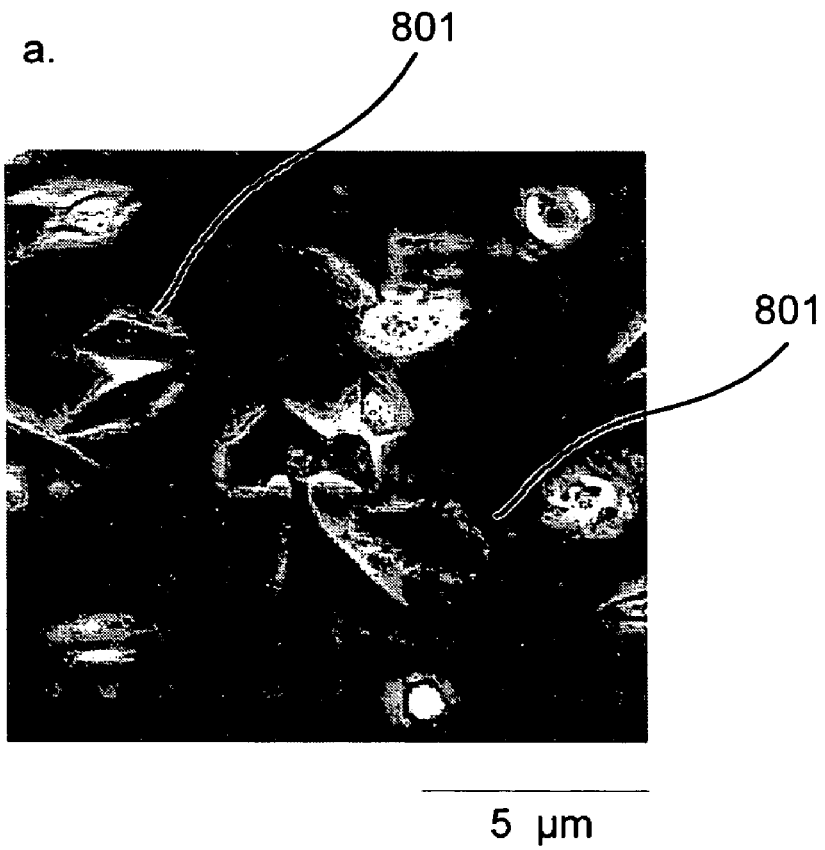
FIGS. 8*a* and 8*b* are micrographs at two magnifications demonstrating ultrasound assisted delivery of Sudan Black to endothelial cells.
Figure 8:
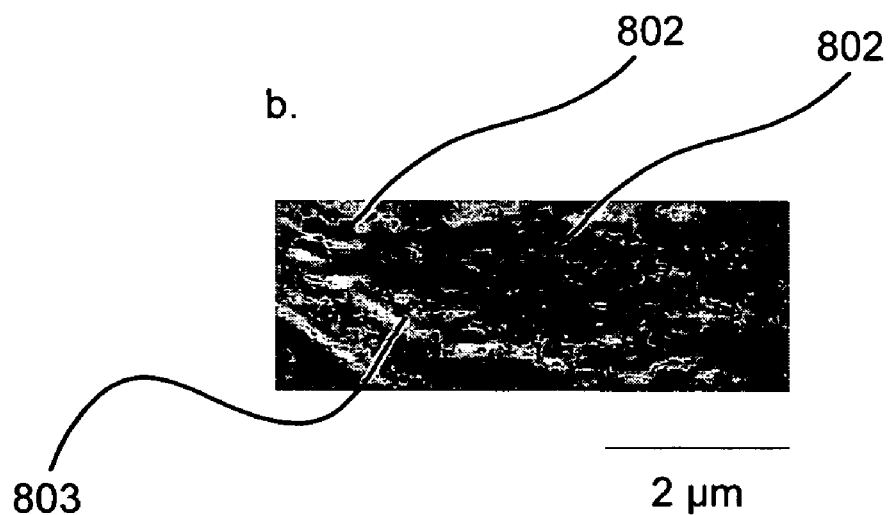

Liposphres containing paclitaxel in soybean oil have been studied for concentration, size, acute toxicity in mice, and acoustic activity and drug release with ultrasound. E C Unger, T P McCreery, et al. *Invest Radiol.* 33(12):886-892 (Dec. 1998) (the entire disclosure of which is hereby incorporated by reference in its entirety for all purposes). We have shown that the substantially lower viscosity of triacetin greatly improves the oscillation, radiation force susceptibility, and fragmentation potential of AALs at low acoustic pressures (D. May, J. Allen, and K. W. Ferrara, *IEEE Transactions on UFFC,* 49(10):1400-1410 (October 2002); J. Allen, D. May and K W Ferrara, *Ultrasound in Medicine and Biology,* 28(6):805-816 (July 2002)), but the data in Unger, et al. (December 1988) demonstrate the in vivo proof of concept and low toxicity. Additional acute toxicity studies with AALs containing triacetin are underway, however many other low-viscosity oils may be used in the practice of the invention, and triacetin is frequently used for other therapeutic purposes. Currently preferred for practicing the invention are oils having kinematic viscosities on the order of about 10 mm²/sec to about 80 mm²/sec at 37° C. Liposphres containing Sudan Black dye were produced to demonstrate the acoustically-active liposphere (AAL) ultrasound release concept (Unger, et al. (December 1988)). FIG. 7 shows the results from an experiment in which mice were injected with AALs containing Sudan Black and shows that there is increased deposition of the dye in the region of tissue subjected to insonation. AALs with Sudan Black are also shown to adhere to endothelial cells in a flowing system in FIGS. 8a and 8b. Endothelial cells 801 were plated within polyester tubing. AALs labeled with Sudan Black were injected at a velocity on the order of several millimeters per second. An ultrasound pulse sequence consisting of radiation force pulses followed by destruction pulses was applied. AAL fragments 802 are shown adherent to cell 803. FIG. 8b is a higher magnification image of a section of the image shown in FIG. 8a. Acute toxicity studies in mice showed a 10-fold reduction in toxicity for paclitaxel in AALs compared with free paclitaxel (anger, et al. (December 1988)). The AALs reflected ultrasound and can be monitored in vivo using their echoes. Increasing amounts of ultrasound energy selectively ruptured the AALs and released the paclitaxel.

Using ultrasound energy, drugs encapsulated in drug delivery vehicles on the order of several microns can be fragmented into small particles on the order of ten to hundreds of nanometers. These structures may then pass through endothelial cell junctures in tumors and are of a size to be most effective for drug delivery in tumors within other organs. For delivery to endothelial cells in the brain, the paclitaxel may pass through the lipid phase in the membrane. The maximum expansion of the outer radius of the AAL is slightly less than that predicted by theory. The probability of AAL fragmentation increases with decreasing frequency (D. May, J. Allen, and K. W. Ferrara, *IEEE Transactions on UFFC,* 49(10):1400-1410 (October 2002)). For AAL fragmentation, a frequency of 1.5 MHz is very effective, the minimum pulse length is five cycles (id.), and a pressure of 1.6 MPa is required to fragment micron sized agents. A thorough discussion of the assumptions of the model and experiments is presented in D. May, J. Allen, and K. W. Ferrara, *IEEE Transactions on UFFC,* 49(10):1400-1410 (October 2002); and J. Allen, D. May and K W Ferrara, *Ultrasound in Medicine and Biology,* 28(6):805-816 (July 2002).

Example 3

Effect of Radiation Force on Microbubble Agents (Contrast and AAL)

Figure 9:
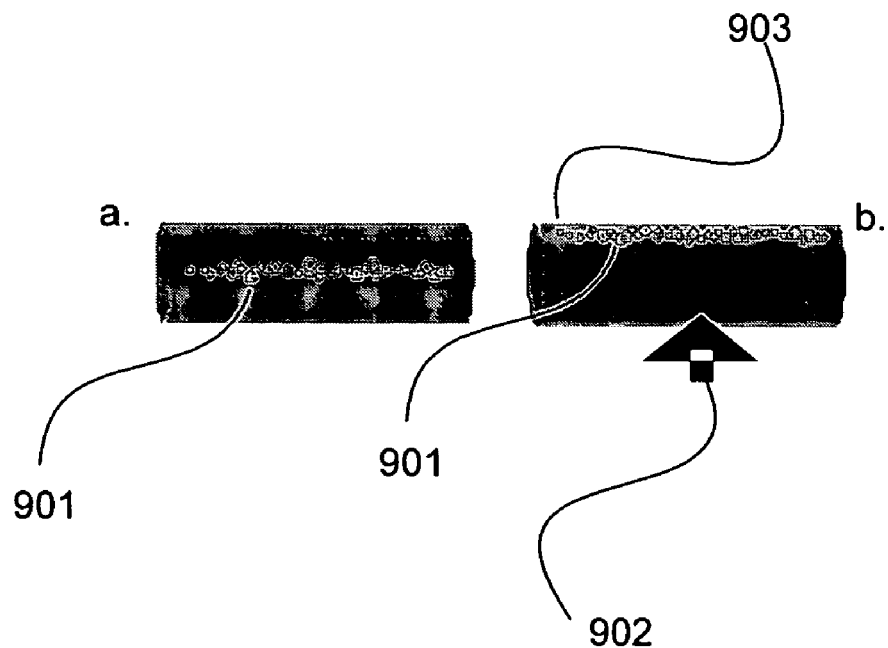
FIG. 9 is a cartoon demonstrating deflection of carriers with ultrasound pulsing within a vessel.
Figure 10:
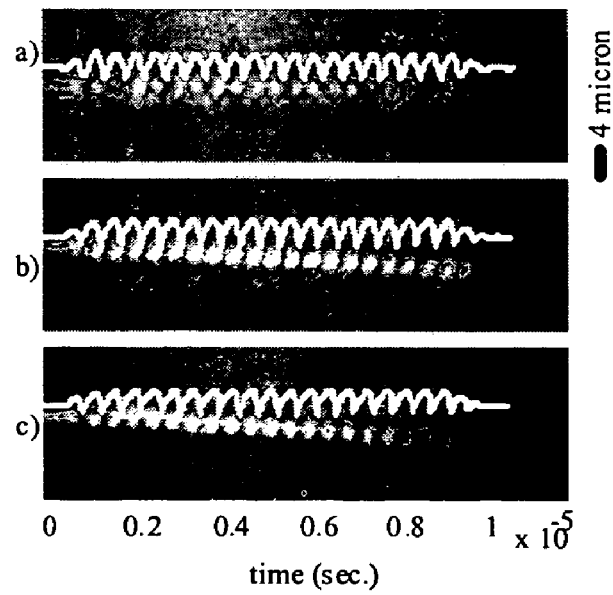
FIG. 10 includes three micrographs showing radiation force on ultrasound contrast agents in vitro.

The effect of acoustic radiation force on contrast agents and AALs has been studied in detail. P. Dayton, K. Morgan, *IEEE Transactions on Ultrasonics, Ferroelectrics, and Frequency Control,* 44(6): 1264-1277 (1997); P. Dayton, "The effects of acoustic radiation force on contrast agents: experimental and theoretical analysis," Ph.D. Dissertation, University of Virginia, August 2001; Paul A. Dayton, John S. Allen, Kathy W. Ferrara, J. Acoust. Soc. Am., 112(5): 2183-2192 (November 2002); 2183-2192; P. Dayton, A Klibanov, G. Brandenburger, K. Ferrara, *Ultrasound and Medicine and Biology,* 25(8):1195-1201 (1999) (the entire disclosures of which are hereby incorporated by reference in their entirety for all purposes). For small, highly compressible objects, such as contrast agents and AALs, we have demonstrated that the radiation force, produced by insonation with a pressure of 100 kHz, and duty cycle <0.1%, can result in rapid translation of the contrast agents and AALs. With optimized parameters, the acoustic field produced by a clinical transducer produces translation of the agents away from the acoustic source. In addition, secondary radiation force produces an attractive force between the agents, causing the bubbles to aggregate. We have thoroughly documented these effects and their relation to acoustic parameters, and in addition, have developed a theoretical model that accurately simulates the displacement of individual bubbles over an acoustic pulse. A cartoon demonstrating the effect of primary radiation force in deflecting the path of carriers is shown in FIG. 9. FIG. 9a depicts a streamline of carriers 901 before the application of ultrasound pressure. Following application of ultrasound pressure (indicated by arrow, 902, the streamline is displaced to the vessel wall 903 (FIG. 9b). While incompressible objects experience a radiation force and effective displacement that increases with center frequency, compressible objects driven at their resonant frequency experience a far greater displacement. With each acoustic cycle, the AAL or contrast agent expands and contracts, and also can experience a net translation. This phenomenon is illustrated in FIG. 10 using radiation force on an ultrasound contrast agent in vitro with a 20-cycle pulse at a center frequency of 2.25 MHz and a pressure of 180 kPa for a 2.4 μm (FIG. 10a), 1.7 μm (FIG. 10b) and 1.5 μm (FIG. 10c) resting radius agent. Note the contrast agent oscillates and translates a small amount with each acoustic cycle. Transmitted waveform is shown in white.

Figure 11:
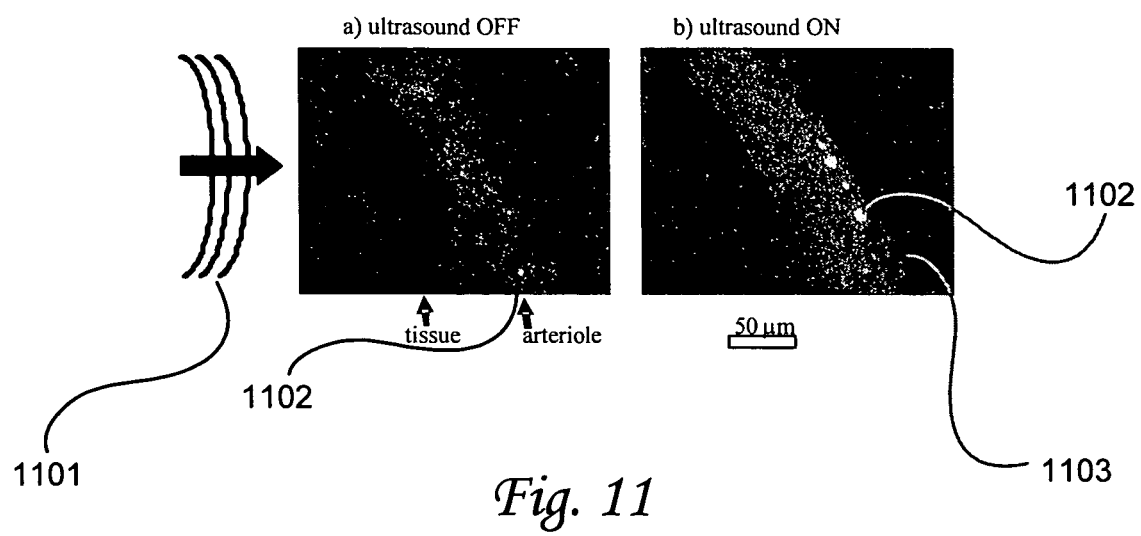
FIG. 11 shows two micrographs demonstrating radiation force in vivo using fluorescently labeled contrast agent with intra-vital microscopy.

We have generated videotaped sequences of the insonation of AALs and contrast agents. First, we have shown the results of applying a sequence of pulses that deflect AALs to the vessel wall, then fragment the agent, and finally allow the replenishment of agents within the region before repeating the pulse sequence. This vessel diameter is approximately 1 mm in this case. The videos also demonstrate the effect of radiation forces on contrast agents within full hematocrit flowing blood and during intra-vital microscopy. No difference was observed in the spatial displacement of contrast agents when flowing in a vessel containing blood as compared with agents flowing in saline. The effect of radiation force in vivo using intravital microscopy was also summarized in P. Dayton, "The effects of acoustic radiation force on contrast agents: experimental and theoretical analysis," Ph.D. Dissertation, University of Virginia, August 2001, and P. Dayton, A Klibanov, et al. (1999) is illustrated in FIG. 11, where we illustrate that the ultrasonic field (diagrammed as 1101) causes fluorescently-labeled contrast agents 1102 to localize along the wall 1103 of a 50-micron arteriole in a mouse cremaster muscle. FIG. 11a is an image obtained with ultrasound off. FIG. 11b is an image obtained with ultrasound on.

When agents are concentrated near a vessel wall, they travel at a reduced velocity compared to those in the center of the flow stream. Agents 1102 shown along the wall 1103 of the vessel in FIG. 11b are traveling at a velocity less than 1 mm/second, whereas the velocity in the center of the vessel was estimated at 7.5 mm/second. We also observe in FIG. 11b that radiation force causes the agents 1102 to attract each other, resulting in a much larger concentration of microbubbles along the vessel wall 1103 than might otherwise occur. These agents do not fuse and the attraction is completely reversible.

Example 4

Translation of the Carrier

In Paul A. Dayton, John S. Allen, et al. (November 2002), we developed a model for the displacement produced by radiation forces acting on a contrast agent, and this model is reviewed below. The translational motion of a microbubble in a fluid during insonation is calculated by solving a particle trajectory equation, represented by Eq. 5.

$$m_b(t)a_b(t) = F_{RF}(t) + F_{QS}(t) + F_{AM}(t) + F_{RB}(t) + F_H(t) \qquad (5)$$

Such an equation may be derived from first principles for an unsteady Stokes flow around a rigid sphere. The reader is referred to the text by Brennen (C. E. Brennen, *Cavitation and bubble dynamics*, Oxford University Press (1995) (the entire disclosure of which is incorporated by reference in its entirety for all purposes)) for a more comprehensive review of the bubble and particle motion in fluids. The term, $m_b a_b$, is the product of the mass of the bubble and its acceleration. For convenience, the mass of the bubble is expressed as $\rho_b V_b$, since it is easier to physically estimate the density and volume of a bubble than its mass. Thus, the term on the left may be expressed as $$\rho_b V_b \frac{du_b}{dt}$$

where $u_b$ is the velocity of the bubble.

The radial oscillations of the contrast agent determined from (3) above enter (5) in the term $F_{RF}(t)$, with the radial oscillations used to predict the volume as a function of time. $F_{RF}(t)$ is the radiation force produced by the acoustic pressure wave. The acoustic radiation force on a highly compressible bubble much smaller than the acoustic wavelength has been derived by previous researchers (L. A. Crum, A. I Eller, *Office of Naval Research Technical Memorandum*, No. 61, (1969); V. N. Alekseev, *Soviet Physics, Acoustics*, 29(2): 77-81 (1983); A. Prosperetti, *Ultrasonics*, 22(3):97-144 (1984) (the disclosures of which are hereby incorporated by reference in their entirety for all purposes)). The instantaneous radiation force in the direction of acoustic propagation is equal to $$V \frac{dP_l}{dx},$$

where V is the volume of the bubble and $$\frac{dP_l}{dx}$$

is the pressure gradient in the liquid (spatially varying in the x direction only). The second term, $F_{QS}(t)$, is the quasi-static drag force. This term represents translational drag on the bubble from the viscosity of the fluid. One established form of this term is $$\frac{1}{2} \rho_l |u_r| u_r A C_d,$$

where A is the cross-sectional bubble area, and $u_r$ is the relative velocity between the translating bubble and the liquid. Empirical approximations of this term have been determined by researchers for air bubbles of different sizes under various conditions V. E. Johnson and T. Hsieh, *Sixth Naval Hydrodynamics Symposium*, pp. 163-182 (1966); L. A. Crum, *J. Acoust. Soc. Am.*, 57: 1363-1370 (1975); T. Watanabe and Y. Kukita, *Physics of Fluids A*, 5(11):2682-2688 (1993) (the entire disclosures of which are hereby incorporated by reference in their entirety for all purposes), and we use values determined by Meyer, et al. *Transactions of the ASME*, 114:672-679 (1992) (the entire disclosure of which is hereby incorporated by reference in its entirety for all purposes). The value of $u_r$ is defined as the difference between the bubble velocity and the liquid velocity, $u_r = u_b - u_l$. The liquid velocity, $u_l$, is in this case determined from the acoustic pressure field (H. J. Rath, *Acustica*, 44:148-155 (1980) (the entire disclosure of which is hereby incorporated by reference in its entirety for all purposes).

$$\frac{\partial u_l}{\partial t} = -\frac{1}{\rho_l} \frac{\partial P}{\partial x} \tag{6}$$

$C_d$ is the drag coefficient, and there are several empirical formulations for this value discussed in the literature. Both Meyer et al. and Johnson and Hsieh (R. S. Meyer, M. L. Billet, J. W. Holl, "*Transactions of the ASME*, 114: 672-679 (1992); V. E. Johnson and T. Hsieh, *Sixth Naval Hydrodynamics Symposium*, pp. 163-182, (1966)) use the expression $$C_d = \frac{24}{Re_b}(1 + 0.197 Re_b^{0.63} + 2.6 \times 10^{-4} Re_b^{1.38}) \tag{7}$$

$$\text{where } Re_b = \frac{2R|u_l - u_b|}{v} \tag{8}$$

The third term on the right in Eq. 5, $F_{AM}$, is known as the added mass. The unsteady translation of the bubble in a fluid requires acceleration of the fluid. Adding the mass of the fluid to the true mass of the bubble incorporates this effect into the force balance. This term describes the force that must be exerted in order to accelerate a rigid sphere in the surrounding fluid, and is commonly expressed in the literature as Eq. 9:

$$F_{AM} = \frac{1}{2} V \rho_l \left( \frac{du_l}{dt} - \frac{du_b}{dt} \right) \tag{9}$$

$F_{RB}$ is an additional added mass term used by Meyer et al. which takes into account the additional acceleration due to the oscillating bubble wall. This term is expressed as in Eq. 10:

$$F_{RB} = \frac{3}{2} \frac{\rho_l V_b}{R} (u_l - u_b) \frac{dR}{dt} \tag{10}$$

Several researchers have shown that the history term, $F_H$, provides only a small (5%) contribution to the total drag on a translating bubble. Since the effect is small, and the history term is computationally intense, this term was neglected from our model. Finally, we add a term to account for the effect of buoyancy and friction due to the vessel wall on the agent. In summary, the differential equation used to solve for the motion of a bubble translating due to acoustic radiation force can be given by Eq. 11.

$$\rho_b V_b \frac{du_b}{dt} = -V \frac{dP_l}{dx} + \frac{1}{2} \rho_l |u_r| u_r A \frac{24}{\frac{2R|u_l - u_b|}{v}}$$

$$\left(1 + 0.197 \left(\frac{2R|u_l - u_b|}{v}\right)^{0.63} + \right. \tag{11}$$

-continued $$\left. 2.6 \times 10^{-4} \left(\frac{2R|u_l - u_b|}{v}\right)^{1.38}\right) +$$

$$\frac{3}{2} \frac{\rho_l V_b (u_l - u_b)}{R} \frac{dR}{dt} + \frac{1}{2} \rho_l \frac{d}{dt}(V(u_l - u_b) +$$

$$(V(\rho_l - \rho_b)g - \mu R^2 (u_l - u_b)^2 \rho_l) \mu_F$$

Example 5

Figure 12:
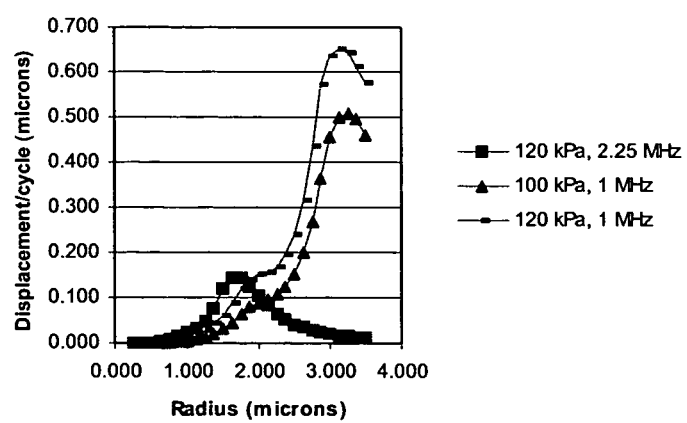
FIG. 12 is a graph showing predicted displacement of ultrasound contrast agent.
Figure 13:
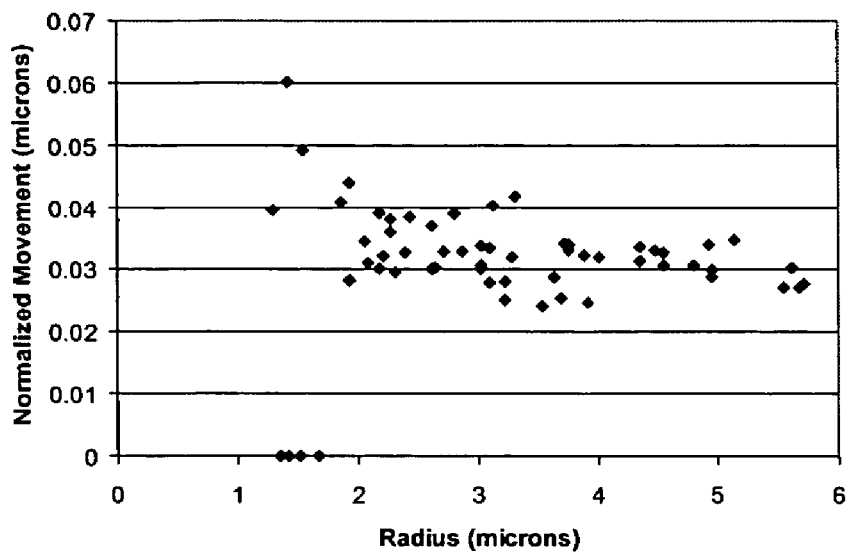
FIG. 13 is a graph of experimentally measured displacement of AALs normalized to microns/cycle.

Experimental Data for Translation with Radiation Force Compared with Predictions The predicted displacement of ultrasound contrast agents in response to low amplitude ultrasonic pulses is summarized in FIG. 12, and both the predictions and experimental data with a similar displacement are summarized in Paul A. Dayton, John S. Allen, Kathy W. Ferrara, (November 2002). FIG. 12 shows that the peak displacement (and the peak primary radiation force) occur for agents with a radius that is near the resonant size for the insonating frequency. Larger agents, resonant near 1 MHz, demonstrate a peak displacement on the order of 0.6 cycles/micron. The peak displacement for MP1950 (a lipid-shelled agent) insonated at 2.25 MHz is approximately 0.1 microns/cycle, and occurs for a resting radius of approximately 1.7 microns (corresponding to resonance). Experimental data (FIG. 13) shows that AALs with a specific lipid/triacetin ratio (corresponding to the formulation with 750 µl of added triacetin as described in Example 7, below) can be translated approximately 0.04 microns/cycle (thus slightly less than the contrast agent) at a center frequency of 2.5 MHz and pressure of 200 kPa. The peak displacement of AALs typically occurs at higher frequencies (2.5-5 MHz) than the contrast agents. Other formulations are translated substantially less (on the order of 0.001 microns/cycle). It is within the level of ordinary skill for an artisan having the benefit of this disclosure to compare formulations and derive optimized parameters.

Assuming that the great majority of AALs reside in capillaries, it is sufficient to displace the carrier on the order of microns, and therefore a cycle count on the order of thousands of cycles is sufficient. In other embodiments, i.e., for treatment of cardiovascular disease, the AALs are to be translated a distance on the order of hundreds of microns to provide therapy to small arteries and veins as well. Acoustic pressures as low as 50 kPa are effective in producing such a displacement.

We have shown in Paul A. Dayton, John S. Allen, Kathy W. Ferrara, (November 2002) that the greatest radiation force magnitude on an AAL occurs for a transmitted frequency equal to the resonant frequency of the gas bubble (2.5-5 MHz). Typical parameters for a gas-filled agent include a transmitted center frequency between 2.5-6 MHz, a transmitted pressure of 50-200 kPa, pulse length of 20 or more cycles, and a pulse repetition rate of tens of kHz (i.e., typical Doppler parameters). For AALs, ideally the vehicle is first deflected to the wall, and then fragmented once a sufficient set of radiation force cycles has been applied. The pulse sequencing required is complex but easily achieved by an ordinarily skilled artisan having the benefit of this disclosure.

Example 6

Research Design and Methods

To deliver drugs to the brain, we choose one of several new strategies to combine permeability enhancement with a traditional chemotherapeutic. The ultrasonic pulses can be characterized as those required for displacement to the vessel wall, and those required for fragmentation of the vehicle with a transfer of the compound within the vehicle to surrounding cells desired. We first develop a model for the translation of drug delivery vehicles in response to a pulsed ultrasonic field, and compare this with experimental data acquired over a range of pressures. Delivery vehicles incorporating paclitaxel in a fluorescently and radionuclide-labeled form are created. The efflux of the labeled paclitaxel from these vehicles is estimated with varying ultrasound parameters. A co-culture of endothelial and glial cells is used to evaluate changes in permeability of the BBB to the proposed therapies. Finally, F18-Fluoropaclitaxel is used to assess the local concentration of paclitaxel in vivo.

Example 7

Acoustically Active Lipospheres Containing Labeled Paclitaxel

One to five weight percent (w:w) lipid mixture (dipalmitoylphosphatidylcholine [DPPC], dipalmitoylphosphatidic acid [DPPA], and dipalmitoylphosphatidylethanolamine-polyethyleneglycol-5000 [DPPE-PEG-5000], in molar ratio of 82:10:8) is suspended in normal saline followed by heating briefly to 60° C. and then subjected to a series (n=4) of freeze-thaw cycles. The formulation is then dried in vacuo followed by re-suspension in a diluent comprising normal saline, glycerol, and propylene glycol (8:1:1, v:v:v). To 1.14 mLs of the 6.35 mg/mL lipid formulation is added 320-750 microliters of triacetin oil. The formulation is then shaken on a vortex shaker (Espe Shaker, Munich, Germany) at approximately 4500 rpm for 45 seconds to yield acoustically-active lipospheres. Acoustically-active lipospheres are sized and counted on a Particle Sizing Systems optical sizer (Particle Sizing Systems, Santa Barbara, Calif.).

Example 8

Formulation of AALs with Paclitaxel and Testing In vitro

Paclitaxel (labeled with fluorescence or F18) is added to the AAL. Briefly, 1-5 weight % of chemotherapeutic compound relative to the lipid is added to the lipid formulation followed by suspension in normal saline and freeze-thawing. A formulation comprising 1-5 mg mL$^{-1}$ of the lipid/chemotherapeutic mixture is formulated in a diluent comprising normal saline: propylene: glycerol, 8:1:1, v:v:v. To 1.14 mLs of the 6.35 mg/mL lipid formulation is added 320-750 microliters of triacetin oil. The AAL is generated using agitation from the Vialmix shaker (45 seconds).

Example 9

Ultrasound System

A system for enhanced local drug delivery is designed and built. To illustrate proof of concept, the system primarily is capable of delivering radiation force and fragmentation pulses in a small region. A single piston transducer (V305, Panametrics, Waltham, Mass.) with a center frequency of 2.4 MHz, 6 dB bandwidth of 1.6-3.3 MHz, focal length of 2.34", and 0.75" aperture is used for this system. This is a focused transducer that can insonate along a single line of sight. The acoustic pressure is calibrated with a hydrophone (PZT-Z44-0200, Specialty Engineering Associates). For the in vivo experiments, the same focused transducer is used, and is swept over 2D planes for imaging and a small 3D region for therapy using an available motion system.

A 0.2 cm×0.2 cm×0.2 cm (azimuth x elevation x depth) volume is imaged and treated. The 3D imaging is accomplished by mechanically scanning the transducer linearly in elevation and grabbing frames at incremental positions. The focused transducer is linearly scanned in elevation using a combination linear/rotary servo motor (LAR 30-25, SMAC, Carlsbad, Calif.) and a motion controller (DMC-2240, Galil Motion Control, Rocklin, Calif.). The treatment phase consists of generating radiation force pulses and within a short time interval delivering high-intensity pulses with the spherically-focused piston transducer. A 2 kW (peak) pulsed-power amplifier (BT02000-CLβ, Tomco Electronics, Australia) combined with an arbitrary waveform generator (33120A, Agilent Technologies, Palo Alto, Calif.) is used to drive the piston.

A pulse sequence is created for combined radiation force imaging and AAL destruction. This includes one very long radiation force pulse consisting of approximately 100-10$^6$ cycles at a center frequency between 1.5 and 3.5 MHz and an amplitude between 50-400 kPa, followed immediately by a destruction pulse with an amplitude of 1.6 MPa and a frequency between 1-1.5 MHz. The sequence is repeated once every three seconds. All AALs within the sample volume flowing with a velocity below 1 cm/s are deflected to the wall of a 1 mm vessel with this pulse sequence. At higher velocities, the displacement of agents is less, and therefore a smaller fraction of the agents in a vessel will be deflected to the wall but the effect still is significant. Given that most AALs are resident in capillaries, the sequence is very effective.

Example 10

Development and Evaluation of Model for Radiation Force on AALs and the Resulting Translation The model for the translation of a microbubble in an acoustic field described above is extended to AALs by adding the mass of the oil layer with the appropriate volume as an additional layer in the appropriate terms. The resulting predictions for the displacement of the AAL is compared with experimental data acquired with frequencies between 1.5-3.5 MHz, pulses with 100-10$^6$ cycles, and acoustic pressures between 50 and 400 kPa. The results are compared for formulations with 320-750 microliters of triacetin.

Analysis of R-t curves: Streak images, obtained with a high speed electronic camera (capture rate~10$^9$ frames/sec), are digitized offline using Adobe Photoshop (Adobe) and MATLAB, and converted to radius-time curves. These radius-time curves describe the bubble's response to an acoustic pulse, and are useful in calculating the magnitude of radiation force applied to the AALs. Analysis of the radius-time curve provides expansion ratio and the estimate of the volume as a function of time. As noted earlier, the instantaneous radiation force in the direction of acoustic propagation is equal to $$V \frac{dP_i}{dx},$$

and therefore the instantaneous volume must be estimated and integrated over the pulse. The timing sequence of the seven frame images is positioned to determine if AAL fragmentation occurs due to the acoustic pulse. This analysis allows determination of optimal acoustic parameters for insonation of vehicles. In summary, acoustic parameters optimized to maximize displacement are chosen for the radiation force pulses, and maximum expansion-fragmentation for the fragmentation portion of the sequence.

Example 11

Evaluation of Dye Efflux from AALs

Dynamic studies of delivery to endothelial cells using AALs: The therapeutic capacity of AALs is quantified using ultrasound to enhance delivery of lipid-soluble dyes to endothelial cells. BODIPY FL paclitaxel (Molecular Probes, Eugene, Oreg.) which stains lipid membranes is dissolved in the AAL shell. HUVEC cells are grown on Thermonox coverslips (Nalge Nunc, Rochester, N.Y.), which are nearly acoustically transparent. The coverslips are used as one side of a static assay chamber with a total volume of approximately 500 µL. AALs diluted with phosphate buffered saline ("PBS") to concentrations of 10, 100, and 1000 bubbles per µL are injected into the assay chamber. The chamber then is placed on an acoustic standoff in a water-filled chamber. Acoustically absorbent material lining the chamber prevents multiple reflections. The chamber is insonified with the pulse sequences and the ultrasound system described above. After insonation, the coverslips are removed and observed optically with a fluorescence microscope (IX70, Olympus, Melville, N.Y.) to determine delivery of staining to endothelial cells. Amount and location of stain uptake is quantified as a function of acoustic frequency, acoustic pressure, and duty cycle. Experiments also are performed under control conditions, i.e., in the absence of ultrasound with the AALs incubated with the cells.

Example 12

Flowing Assays of Drug Transfer with Ultrasound Radiation Force

Figure 14:
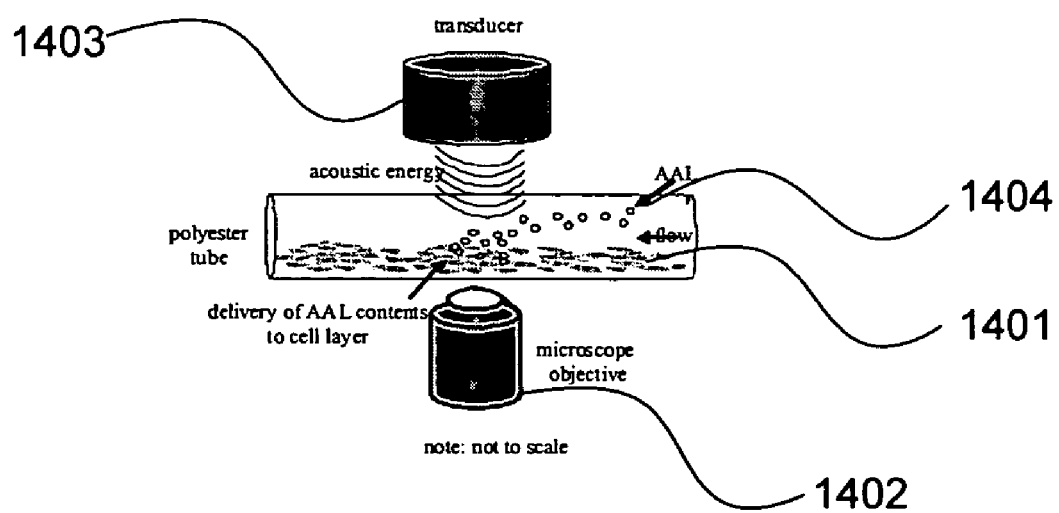
FIG. 14 is a diagram of the flowing experimental system.

A dilute solution is pumped through a 1 mm polyester tube in which cells 1401 are cultured to form a vessel mimetic. Flow is controlled by a syringe pump. The tube is positioned in a water bath chamber, where it is placed at the mutual focus of both the objective 1402 and ultrasonic transducer 1403 (FIG. 14). The polyester is nearly optically and acoustically transparent. Acoustic radiation force is produced with the ultrasound transducer 1403 as described above, and is used to direct the flowing carriers 1404 towards the cell layer 1401. (Molecular Probes provides three fluorescent derivatives of paclitaxel: Oregon Green 488 paclitaxel (Flutax-2, P-22310), BODIPY FL paclitaxel (P-7500) and BODIPY 564/570 paclitaxel (P-7501)). BODIPY FL-paclitaxel is included within the AALs. AALs are injected into the tubing. The pulse sequence shown to be optimal above (and employed in vivo) is evaluated within this flowing model system. The tubing is split open after the experiment. Transfer of the fluorescently labeled drug to the HUVEC cells is quantitatively assessed as a function of flow rate by scanning a fluorimeter across the region and integrating the fluorescence. A preliminary image with Sudan Black as a model compound is shown as FIG. 8.

Example 13

In vitro Evaluation in Endothelial-glial Co-culture

Endothelial-glial co-culture: An in vitro BBB model is used, comprised of endothelial cells and co-cultured glial cells, where the endothelial cells are grown on semi-permeable filter inserts. The cell culture model used in this study has proven to be useful in many recent studies of the BBB (A H. Schinkel, *Adv Drug Deliv Rev.* 36(2-3):179-194 (Apr. 5 1999) (incorporated herein by reference in its entirety for all purposes). The ECV304 cell line (ATCC Europe) shows a robust endothelial phenotype and increases in transendothelial electrical resistance (TEER) when co-cultured with rat C6 glioma cells. In addition, C6 co-cultured with ECV304 cells develop other characteristics of brain endothelium, including the expression of P-glycoprotein. As in Schinkel (1999), the ECV304 cells are grown on inserts over rat C6 glioma cells. We have previously tested BD Falcon™ Cell Culture Inserts and found them to be nearly acoustically transparent, and have created 12-well plates from Rexolite (another nearly acoustically transparent plastic). This is important for these experiments to minimize reflections. C6 cells are suspended in culture medium and then added to wells of a 12-well plate and given 3-4 hours to attach. ECV304-containing inserts are placed in the wells. The supports at the base of the inserts are designed such that there is no physical contact between the C6 cells and the ECV304 cells or the insert membrane. The co-cultured cells are then incubated at 37 degrees C. over 4 days.

The transducer is calibrated while it is focused in the optical field of view with a needle hydrophone (PZT-Z44-0200, Specialty Engineering Associates) and a preamplifier (A17dB, Specialty Engineering Associates). Acoustically absorbent rubber is placed below the sample chamber to prevent multiple reflections.

Assessing permeability of cells to labeled paclitaxel with and without P-gp inhibitor in endothelial-glial co-culture: BODIPY FL paclitaxel within the AALs is used for these experiments as outlined in Table 3. The AALs are added to the wells of the 12-well plates containing the endothelial and co-cultured glial cells and saline is added to couple the ultrasound transducer to the plates. The plates are exposed to acoustic pulses at various combinations of clinically-relevant acoustic parameters to determine their response. The pulse sequences shown to be optimal in the above examples are employed. After 5 seconds, 20 seconds, 1 minutes, 5 minutes, and 20 minutes of insonation, the fluorescence in the saline, endothelial cells, and in the glial cells is assessed and compared to the control unexposed cells. In a separate experiment Valspodar (PSC 833) or control (saline) is added in a concentration of 10 µM with an exposure of 30 minutes to 4 hours. The drug solution is added to the cell culture and the plate is placed on an orbital shaker for 10 minutes. Insonation is performed (or control without ultrasound) and fluorescence in the saline, glial, and endothelial cells is assessed. In addition, the endothelial cell layer is stained to evaluate the junctional expression of the tight junction-associated protein claudin-1, to determine whether the protocol has altered function. To evaluate claudin-1, the endothelial cells are fixed with cold methanol and permeabilized with 0.1% Triton X-100 in PBS. The cells are soaked in the blocking solution and incubated with anti-claudin-1 antibody. The Alexa Fluor 568-conjugated IgG is used as a secondary antibody. Also, P-gp expression is evaluated using the C219 monoclonal antibody.

Test Groups are as Follows and Include a Range of Parameters for Valspodar and ultrasound (US) Exposure:

TABLE 3

| Group | Ther. US | P-gp modulation | AAL |
|---|---|---|---|
| 1 | Yes | Valspodar | AAL containing BODIPY FL-paclitaxel |
| 2 | No | Valspodar | AAL containing BODIPY FL-paclitaxel |
| 3 | Yes | Control | AAL containing BODIPY FL-paclitaxel |
| 4 | No | Control | AAL containing BODIPY FL-paclitaxel |

Transendothelial electrical resistance (TEER) is used to quantify basal and simulated drug-induced changes in small ion permeability of the in vitro BBB. Measurement of the TEER is performed using a resistance measuring chamber (Endohm chamber and EVOM ohmmeter, World precision instruments, Sarasota, Fla.). Inserts are placed between the silver-silver electrodes and the meter is used to record TEER. Resistance is inversely proportional to small ions permeability. Control measurements from blank inserts are subtracted to remove the background. It is important to verify TEER as it indicates a change in the permeability to particles based upon a separate mechanism.

Example 14

Ultrasound Therapy Followed by PET Imaging of Region

Eight groups of mice are studied with and without therapeutic ultrasound as shown in Table 4. This determines the extent to which local delivery of paclitaxel is increased with the use of local delivery of a chemotherapeutic. An effective dose of 20 mg/kg of paclitaxel (in the AAL) is applied followed by therapeutic ultrasound. Therapeutic ultrasound is applied for a period determined following the injection of the drug/control using parameters determined during the in vitro study. We insure that the circulating AALs are eliminated prior to PET imaging with the use of sufficient insonation. The potential for tissue heating is determined using standard methods once the pulse sequence is finalized. The low pressures used in the radiation force pulses (far less than clinical maximum) minimize heating. PET imaging is then performed immediately after this treatment over a period of 30 minutes.

For PET imaging, mice are anesthetized by placing each mouse into an induction chamber and introducing aerosolized isoflurane through a system of tubes into the chamber. Once asleep, the mouse is removed from the chamber and anesthesia maintained through a mask and inhaled doses of isoflurane are titrated to the required anesthetic depth. This provides an excellent plane of anesthesia for at least one hour. Depth of anesthesia is monitored by checking the breathing pattern and by continuously recording blood oxygen saturation via pulse oximetry. Body temperature is maintained via a system of heat lamps and water bottles. Ultrasound is coupled to the skull through a gel pad. The tail vein is catheterized using a 24 gauge indwelling catheter and the AAL is injected as a bolus through the tail vein. Ultrasound is applied to a 0.2×0.2×0.2 mm region in the midline of the coronal and sagittal planes at a depth of 0.2 mm from the surface of the skull. The subsequent PET images are used to determine the extent to which F18-fluoropaclitaxel is delivered to the insonated region, through comparison of the image of the insonated region at the 30 minute time point to that of the surrounding brain. PET images acquired at the 30 minute time point (post-ultrasound) are most useful in the determination of whether ultrasound changes the distribution of F18-fluoropaclitaxel.

TABLE 4

| | | Study groups | | |
|---|---|---|---|---|
| Group | Ther. US | Oral dose | Inject | N |
| 1 | Yes | Valspodar | AAL containing F18-Fluoropaclitaxel | 11 |
| 2 | No | Valspodar | AAL containing F18-Fluoropaclitaxel | 11 |
| 3 | Yes | Control | AAL containing F18-Fluoropaclitaxel | 11 |
| 4 | No | Control | AAL containing F18-Fluoropaclitaxel | 11 |
| 5 | Yes | Valspodar | Intravenous F18-Fluoropaclitaxel | 11 |
| 6 | No | Valspodar | Intravenous F18-Fluoropaclitaxel | 11 |
| 7 | Yes | Control | Intravenous F18-Fluoropaclitaxel | 11 |
| 8 | No | Control | Intravenous F18-Fluoropaclitaxel | 11 |

Valspodar (Novartis Pharmaceuticals (Basel, Switzerland)): Drinking solution containing 100 mg/ml Valspodar is diluted to a concentration of 5 mg/ml with its vehicle, a mixture of Cremophor RH40, ethanol, d,L-α-tocopherol, propylene glycol, and Labrafil M2125CS. A volume of 0.2 ml is administered by oral gavage per 20 g of body weight, resulting in a dosage of 50 mg Valspodar per kilogram of body weight. In the same manner, the vehicle is administered to the control animals.

Sample size justification: In our hands, PET studies demonstrate a 10% standard deviation. For two-sided tests with alpha of 0.05, eleven animals are required in each group to detect a 20% change in therapeutic efficacy at a power of 0.9 for imaging studies that have been shown to demonstrate a standard deviation of 10%.

Synthesis of F18-FPac: Methods for the synthesis of F18-Fluoropaclitaxel have previously been described (D O Kiesewetter, E M Jagoda, et al., *Nucl Med Biol.* 30(1):11-24 (January 2003) (incorporated by reference in its entirety for all purposes)) this method is followed here.

PET: The radiolabeled particles (AALs) containing F18-Fluoropaclitaxel are injected through a catheter as a bolus injection into the tail vein of the rat. Typically, 50-100 microCi of radiolabeled particles are injected, although acceptable images can be achieved with as little as 10-30 microCi. To dilate the tail vein to assist in tracer injection, a heating lamp and/or warm water are used. The activity in the syringe before and after injection is measured in a dose calibrator and corrected for decay so that the injected dose is known. After injection of the particles and initial ultrasound studies the anesthetized animal is positioned on a custom-built bed in the microPET scanner. The bed has an attachment that delivers anesthesia to the animal and is heated by recirculating warm water to maintain the animal's body temperature. Body temperature is monitored throughout the study using a rectal probe. Data is acquired in list mode for a period of 30 minutes. This dataset can be rebinned post-acquisition into user-defined time intervals to create a dynamic sequence of images that show the kinetics. All data are reconstructed with a validated statistical 3-D reconstruction algorithm. Corrections for detector normalization, random coincidences and dead time are applied. No corrections are currently made for photon attenuation or scatter, as these are relatively small effects, and the complexity of the corrections is in our opinion not justified in this setting. Absolute quantification is achieved by calibrating the mouse images with the image of a cylinder containing a uniform concentration of positron-emitting radionuclide with approximately the same geometry and volume as a rat. The calibration scan is acquired under identical conditions and reconstruction parameters as the mouse scan.

Gold standard measurement: Mice are sacrificed following PET imaging, blood and tissues are removed and weighed, and the radioactive content of the brain in the ultrasound treated and untreated regions (as assessed by the location) are assessed and expressed as differential uptake ratio.

Example 15

Elegra Drug Delivery Sequence Implementation

A clinical ultrasound system, the Siemens Elegra, was used to deliver a sequence of radiation force—fragmentation pulses in vitro. The system runs software that allows control of the timing, spatial extent, and intensity of each pulse in the sequence.

Elegra Sequence Software Description

This software currently works with the 3.5PL28 array transducer. Briefly, the pulse sequence sends ultrasound pulses as follows. First, the scanner sends defocused pulsed Doppler pulses along one line of sight at a high pulse repetition frequency (PRF) for a number of milliseconds defined by the Push Time control. These pulses create radiation force, which drives the delivery vehicles or away from the transducer, towards the cell or vessel wall of interest. Next, the system sends no pulses for a second time period, defined by the Pause Time control. This allows any delivery vehicles that have bunched together due to secondary radiation force effects to relax and flow slightly apart, reducing multi-bubble shielding which might reduce the effects of the break pulses. Finally, the system sends five complete color Doppler frames, used as fragmentation pulses. Each frame consists of a number of lines of sight, and each line of sight consists of a number of pulses set by the Ensemble Size control. The system waits for a time set by Repeat Delay and then repeats until Stop Acquire is pressed. During this time, B-mode imaging of the target can take place if it is desired. The total time taken by the sequence using typical settings is just over 2.5 s+0.5 s+30 s=33 seconds.

The amplitude and frequency of the radiation force and fragmentation pulses can be controlled on the ultrasound system using the Doppler and Color menus, respectively and the imaging frames are controlled with the 2D menu. In one embodiment, the following parameters are used: low-amplitude (1% transmit power), higher-frequency (3.6 MHz), many-cycle (~50 cycles for a gate size of 22.5 mm at 3.6 MHz) pulses for radiation force and high-amplitude (100% transmit power), low-frequency (2.0 MHz), short (~5 cycle) pulses for fragmentation. The individual controls for the software are listed in Table 5.

TABLE 5

Elegra Software Controls

| CONTROL | | VALUES |
|---|---|---|
| Push Time | duration of push (Doppler) pulses, in milliseconds | 250 500 1000 2500 |
| Repeat Delay | time between end of break (Color) frames and start of next push, in seconds | 0/no repeat 1 3 5 7 10 15 20 25 30 40 50 60 |
| Gate Size | size of Doppler gate, in mm | 1.5 2.0 2.5 3.0 3.5 4 5 7.5 10 12.5 15 17.5 20 22.5 |
| Ensemble Size | size of Color ensembles | 6 8 10 12 14 16 20 |
| Pause Time | time between push pulses and break frames, in seconds | 0.1 0.2 0.3 0.4 0.5 0.6 0.7 0.8 0.9 |
| Acquire | button starts push break sequencing, repeating according to the Repeat Delay setting | N/A |
| Stop Acquire | button stops push break sequencing | N/A |
| 2D menu (imaging) | frequency, MHz | 5.1 4.5 4.0 3.4 2.8 |
| 2D menu (imaging) | transmit power, % | 0 to 100 |
| 2D menu (imaging) | depth, cm | set to encompass region to be treated, minimum 6 cm |
| 2D menu (imaging) | focus position, cm | set as close as possible to desired treatment depth |
| 2D menu (imaging) | frame rate, Hz | 0.2, 0.5 . . . maximum possible |
| Color menu (fragmentation pulses) | frequency, MHz | 2.0 2.4 3.0 3.4 4.0 |
| Color menu (fragmentation pulses) | transmit power, % | 0-100 |
| Doppler menu (radiation force pulses): | frequency, MHz | 2.8 3.0 3.6 |
| Doppler menu (radiation force pulses): | transmit power, % | 0, 1 . . . 100 |
| Doppler menu (radiation force pulses): | gate depth, mm | ranges from 0 to 2D depth setting |
| Doppler menu (radiation force pulses): | gate size, mm | same as Gate Size control above |

In one example, the following settings were used: Push Time—2500 milliseconds; Repeat Delay—30 seconds; Gate Size—22.5 mm; Ensemble Size—6; Pause Time—0.5 seconds; 2D menu (imaging): frequency 5.1 MHz, transmit power 0%; depth 6.0 cm; focus position 2.0 cm; frame rate max Hz; Color menu (fragmentation pulses): frequency 2.0 MHz; transmit power 100%; Doppler menu (radiation force pulses): frequency 3.6 MHz; transmit power 1%; gate depth 32 mm; gate size 22.5 mm.

Beam Shaping

Generally the timing of an ultrasound transducer array is adjusted to give a focused beam for the highest possible imaging resolution. In our application of radiation force pulses and fragmentation pulses, we are interested in applying our sequence evenly across a volume of tissue. The Elegra software uses a standard pulsed Doppler pulse for radiation force. Pulsed Doppler is normally applied along only one line of sight and therefore has only a small lateral beam width. To apply the radiation force pulse along a larger area, the software tells the Elegra to focus at a distance of three times the focal distance setting, causing the beam in the region of interest to be larger and more diffuse than it would normally be.

Figure 15:
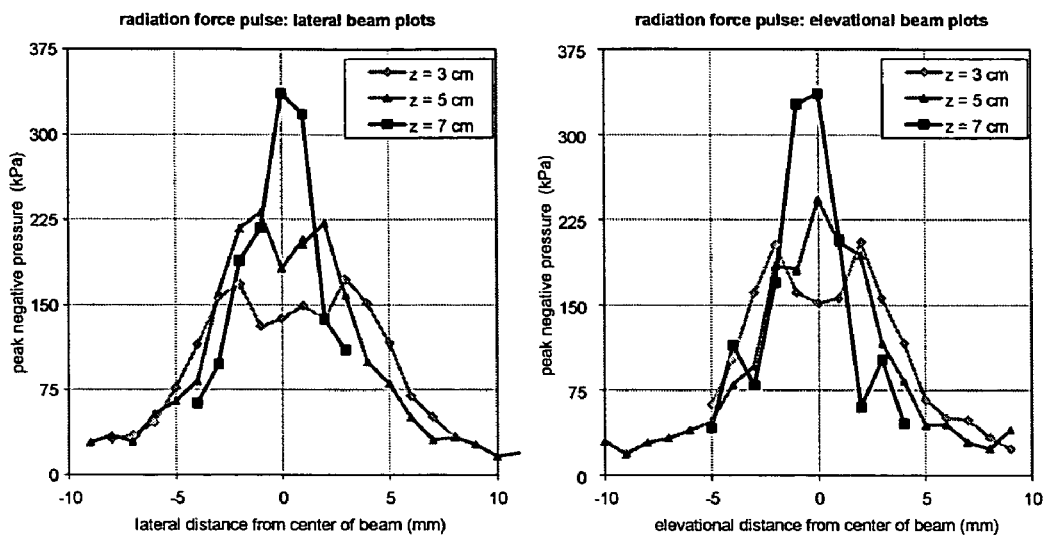
FIG. 15 are radiation force beam plots.
Figure 16:
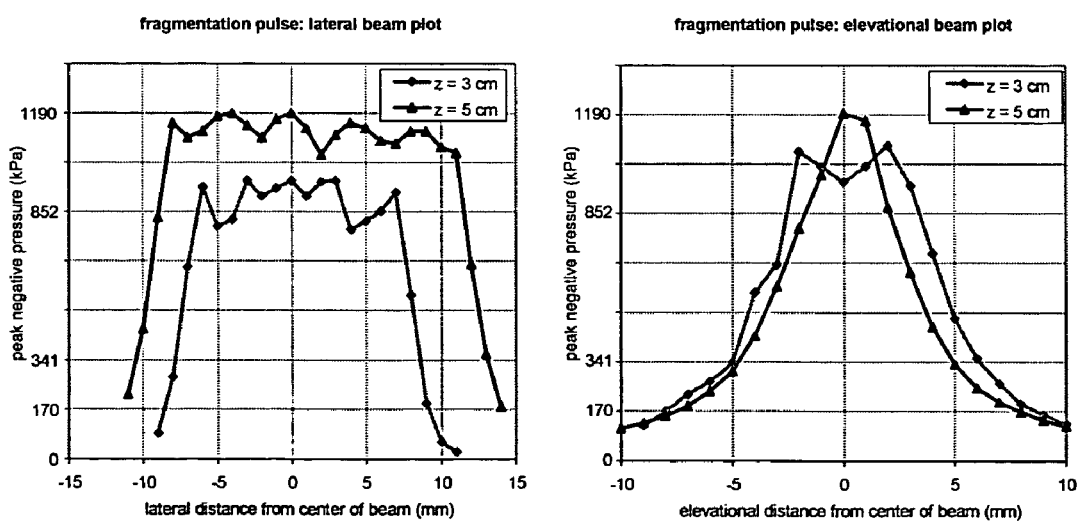
FIG. 16 are fragmentation beam plots.

FIGS. 15 and 16 show beam measurements of the radiation force (FIG. 15) and fragmentation beams (FIG. 16) made using a calibrated needle hydrophone (Specialty Engineering Associates, Soquel, Calif.). The "lateral" direction is parallel to the face of the transducer along the axis of the array; the "elevational" direction is parallel to the face of the transducer and perpendicular to the axis of the array.

The radiation force beam is shown in the lateral and elevational directions at 3, 5, and 7 cm from the transducer: at 3 cm, the distance of interest, the beam has a full width at half-maximum nearing 1 cm in both directions, so the pulse is applied over an area of approximately 1 cm$^2$.

The effective fragmentation region is around 2 cm wide in the lateral direction at 3 cm from the transducer, because the Doppler pulses are fired over several lines of sight.

Figure 17:
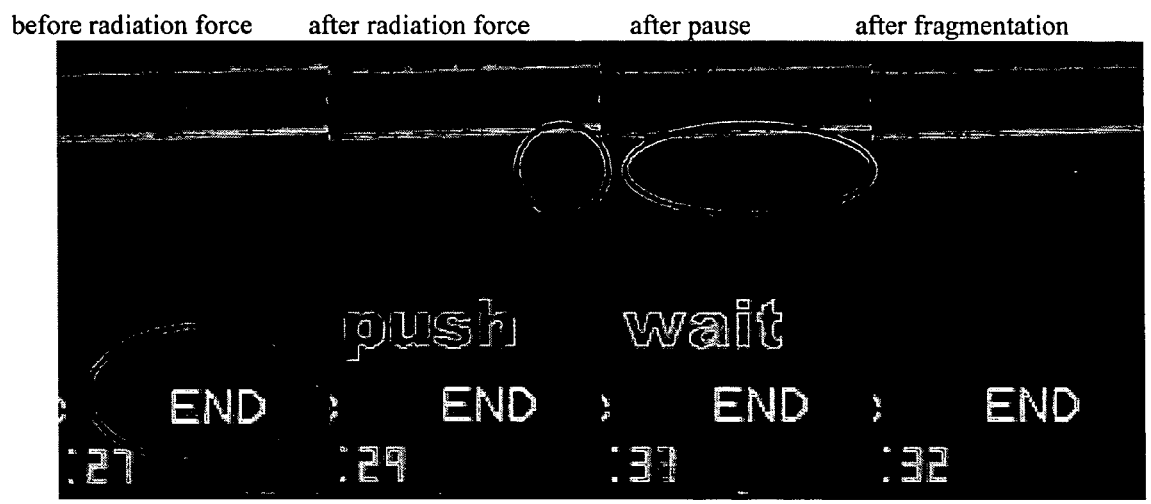
FIG. 17 are micrographs demonstrating the Elegra sequence effect on flowing drug delivery vehicles. Vehicle locations are circled.

The effects of the radiation force—fragmentation sequence on drug delivery agents flowing in a small tube under white-light microscopy was examined. As illustrated in FIG. 17, flowing vehicles were observed to deflect toward the tube wall during the application of radiation force, spread out in the pause between the radiation force and fragmentation pulses, and disappear due to destruction by the radiation force pulse.

Figure 18:
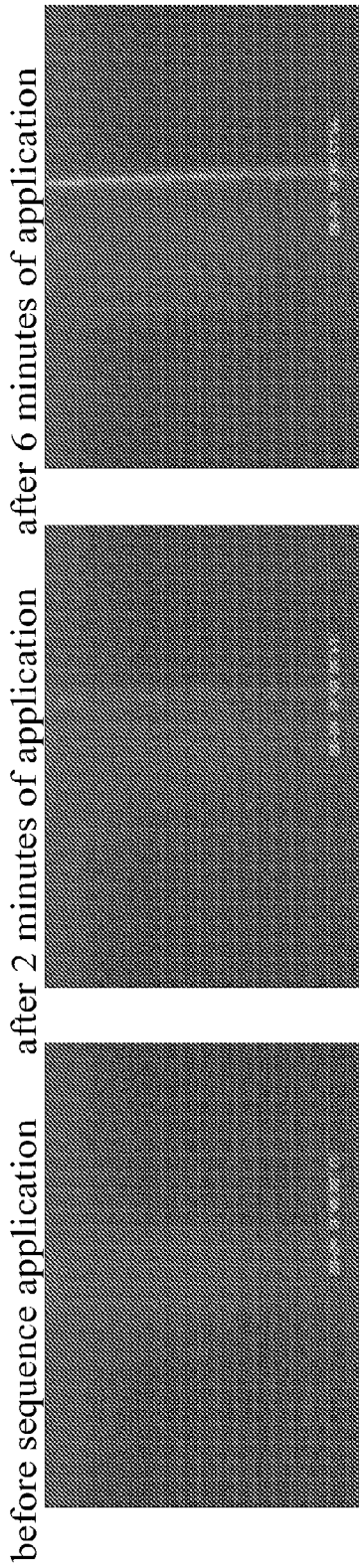
FIG. 18 are epifluorescent images of fluorescent dye delivery to a tube wall.

In a second experiment, fluorescently labeled and biotin-coated drug delivery capsules were injected continuously into an avidin-coated tube. The build-up of fluorescent material on the tube due to the radiation force—fragmentation sequence could be observed, as shown in FIG. 18. The material remained adherent under continued flow through the tube.

Figure 19:
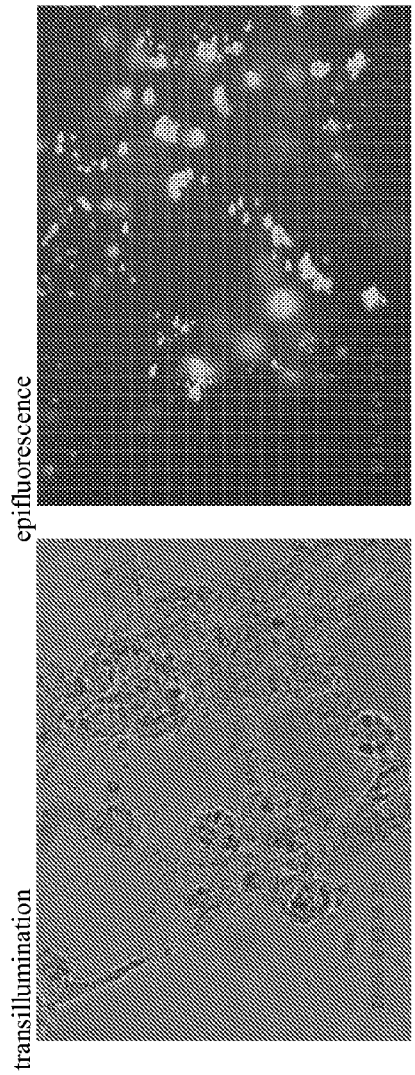
FIG. 19 are microscopy images of dye delivery to cells.

Finally a demonstration of dye delivery from fluorescent-dye-containing drug delivery vehicles to plated cells after application of 10 complete radiation force—fragmentation sequences from the Elegra system was performed. The results are shown in FIG. 19.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method for localized delivery of a compound, comprising:
    administering a carrier, said carrier comprising a therapeutic compound, wherein the carrier is selected from the group consisting of an acoustically active liposphere and a gas-filled agent;
    concentrating said carrier by exposing said carrier to an ultrasound radiation force generated by an ultrasound wave at a first frequency and pressure combination, thereby locally delivering said therapeutic compound, wherein said ultrasound wave at said first frequency and pressure combination concentrates and displaces said administered carrier, but does not rupture said carrier; and
    rupturing said concentrated carrier by insonating said concentrated carrier with an ultrasound wave at a second frequency and pressure combination.

2. The method of claim 1, wherein said first frequency and pressure combination is a combination of a center frequency ranging from 100 kHz to 40 MHz and a pressure ranging from 20 kPa to 6 MPa.

3. The method of claim 1, wherein said second frequency and pressure combination is a combination of a center frequency ranging from 0.1 MHz to 5 MHz and a pressure ranging from 0.3 MPa to 20.0 MPa.

4. The method of claim 3, wherein said second frequency and pressure combination is a combination of a center frequency ranging from 0.8 MHz to 1.8 MHz and a pressure ranging from 0.3 MPa to 2.0 MPa.

5. The method of claim 1, wherein said carrier comprises a polymer, a protein, a lipid, an oil, or a gas.

6. The method of claim 5, wherein the diameter of said carrier is 0.1 μm to 10 μm.

7. The method of claim 6, wherein the diameter of said carrier is 1 μm to 10 μm.

8. The method of claim 7, wherein the diameter of said carrier is 2 μm to 6 μm.

9. The method of claim 1, wherein said administration is into a vessel.

10. The method of claim 9, wherein said vessel is selected from the group consisting of a vein, an artery, a venule, an arteriole, a capillary, and a lymphatic.

11. The method of claim 10, further comprising exposing said vessel to an ultrasound wave at a second frequency and pressure combination sufficient to increase the permeability of said vessel.

12. The method of claim 11, wherein said second frequency and pressure combination is a combination of a center frequency ranging from 0.1 MHz to 5.0 MHz and a pressure ranging from 0.1 MPa to 10 MPa.

13. The method of claim 12, wherein said second frequency and pressure combination is a combination of a center frequency ranging from 0.6 MHz to 2.0 MHz and a pressure ranging from 0.6 MPa to 2.5 MPa.

14. The method of claim 10, further comprising administering an agent that modulates vascular permeability.

15. The method of claim 14, wherein said agent is selected from the group consisting of kallidin, bradykinin, and a prostaglandin.

16. The method of claim 5, further comprising imaging said carrier by receiving ultrasonic emissions from the insonated carrier at a harmonic of said first frequency and generating an image from the received ultrasonic emissions.

17. The method of claim 1, further comprising administering an agent that modulates a function of P-glycoprotein.

18. The method of claim 17, wherein said agent is selected from the group consisting of tamoxifen, valspodar, verapamil, cyclosporine A, and VX-710.

19. The method of claim 1, wherein said carrier further comprises a targeting moiety.

20. The method of claim 19, wherein said second frequency and pressure combination is a combination of a center frequency ranging from 0.1 MHz to 5 MHz and a pressure ranging from 0.3 MPa to 20.0 MPa.

21. The method of claim 20, wherein said second frequency and pressure combination is a combination of a center frequency ranging from 0.8 MHz to 1.8 MHz and a pressure ranging from 0.3 MPa to 2.0 MPa.

22. The method of claim 19, wherein said targeting moiety is selected from the group consisting of an antibody, an antibody fragment, an aptamer, a carbohydrate, a polysaccharide, a peptide, and a small organic molecule.

23. The method of localized delivery of claim 1, further comprising:
wherein said administration is into a vessel; and
exposing said vessel to an ultrasound wave at a second frequency and pressure combination sufficient to increase the permeability of said vessel, wherein said therapeutic compound is locally delivered by extravasating through said increased permeability vessel.

24. The method of claim 23, wherein said permeability increase is not the result of microbubble-induced endothelial cell damage.

25. The method of claim 23, wherein said vessel is selected from the group consisting of a vein, an artery, a venule, an arteriole, a capillary, and a lymphatic.

26. The method of claim 23, wherein said second frequency and pressure combination is a combination of a center frequency ranging from 0.1 MHz to 5.0 MHz and a pressure ranging from 0.1 MPa to 10 MPa.

27. The method of claim 26, wherein said second frequency and pressure combination is a combination of a center frequency ranging from 0.6 MHz to 2.0 MHz and a pressure ranging from 0.6 MPa to 2.5 MPa.

28. The method of claim 23, wherein said carrier comprises a polymer, a protein, a lipid, an oil, or a gas.

29. The method of claim 28, wherein the diameter of said carrier is 0.1 µm to 10 µm.

30. The method of claim 29, wherein the diameter of said carrier is 1 µm to 10 µm.

31. The method of claim 30, wherein the diameter of said carrier is 2 µm to 6 µm.

32. The method of claim 28, wherein said carrier comprises a shell having a thickness>50 nm.

33. The method of claim 32, wherein said carrier shell thickness is>100 nm.

34. The method of claim 33, wherein said carrier shell thickness is>500 nm.

35. The method of claim 28, wherein said lipid or oil has a viscosity at 37° C. between 1 mm$^2$/sec and 100 mm$^2$/sec.

36. The method of claim 35, wherein said lipid or oil has a viscosity at 37° C. between 10 mm$^2$/sec and 80 mm$^2$/sec.

37. The method of claim 36, wherein said lipid or oil has a viscosity at 37° C. between 20 mm$^2$/sec and 60 mm$^2$/sec.

38. The method of claim 23, further comprising imaging said carrier by insonating said carrier with an ultrasound wave at a third frequency and receiving ultrasonic emissions from the insonated carrier at a harmonic of said third frequency and generating an image from the received ultrasonic emissions.

39. The method of claim 38, wherein said third frequency is a center frequency ranging from 0.8 MHz to 20 MHz.

40. The method of claim 23, wherein said concentration is achieved by a mechanism selected from the group consisting of the ultrasound radiation force reducing a flow velocity of said administered carrier, and the ultrasound radiation force displacing said administered carrier to said vessel wall.

41. A method for localized delivery of a compound, comprising:
administering a carrier, said carrier comprising a therapeutic compound, wherein the carrier is selected from the group consisting of an acoustically active liposphere and gas-filled agent; and
concentrating said carrier by exposing said carrier to an ultrasound radiation force generated by an ultrasound wave at a first frequency and pressure combination, thereby locally delivering said therapeutic compound, wherein said ultrasound wave at said first frequency and pressure combination concentrates but does not rupture said carrier; wherein said carrier comprises a polymer, a protein, a lipid, an oil, or a gas and a shell having a thickness>50 nm.

42. The method of claim 41, wherein said carrier shell thickness is >100 nm.

43. The method of claim 42, wherein said carrier shell thickness is >500 nm.

44. The method of claim 5, wherein said lipid or oil has a viscosity at 37° C. between 1 mm$^2$/sec and 100 mm$^2$/sec.

45. The method of claim 44, wherein said lipid or oil has a viscosity at 37° C. between 10 mm$^2$/sec and 80 mm$^2$/sec.

46. The method of claim 45, wherein said lipid or oil has a viscosity at 37° C. between 20 mm$^2$/sec and 60 mm$^2$/sec.

47. The method of claim 41, wherein said second frequency and pressure combination is a combination of a center frequency ranging from 0.1 MHz to 5 MHz and a pressure ranging from 0.3 MPa to 20.0 MPa.

48. The method of claim 47, wherein said second frequency and pressure combination is a combination of a center frequency ranging from 0.8 MHz to 1.8 MHz and a pressure ranging from 0.3 MPa to 2.0 MPa.

49. A method for localized delivery of a compound, comprising:
administering a carrier, said carrier comprising a therapeutic compound, wherein said carrier is selected from the group consisting of an acoustically active liposphere and a gas-filled agent, wherein said administration is into a vessel; and
concentrating said carrier by exposing said carrier to an ultrasound radiation force generated by an ultrasound wave at a first frequency and pressure combination, thereby locally delivering said therapeutic compound, wherein said ultrasound wave at said first frequency and pressure combination concentrates but does not rupture said carrier; wherein said concentration is achieved by a mechanism selected from the group consisting of the ultrasound radiation force reducing a flow velocity of said administered carrier, and the ultrasound radiation force displacing said administered carrier to a wall of said vessel; and
rupturing said concentrated carder by insonating said concentrated carder with an ultrasound wave at a second frequency and pressure combination.

50. The method of claim 49, wherein said second frequency and pressure combination is a combination of a center frequency ranging from 0.1 MHz to 5 MHz and a pressure ranging from 0.3 MPa to 20.0 MPa.

51. The method of claim 50, wherein said second frequency and pressure combination is a combination of a center frequency ranging from 0.8 MHz to 1.8 MHz and a pressure ranging from 0.33 MPa to 2.0 MPa.

* * * * *

UNITED STATES PATENT AND TRADEMARK OFFICE
CERTIFICATE OF CORRECTION

PATENT NO. : 7,358,226 B2  Page 1 of 1
APPLICATION NO. : 10/928648
DATED : April 15, 2008
INVENTOR(S) : Paul Dayton et al.

It is certified that error appears in the above-identified patent and that said Letters Patent is hereby corrected as shown below:

Column 41, Line 46, Claim 32
Please insert a space between the word "thickness" and ">"

Column 41, Line 48, Claim 33
Please insert a space between the word "is" and ">"

Column 41, Line 50, Claim 34
Please insert a space between the word "is" and ">"

Column 42, Line 15, Claim 41
Please insert a space between the word "thickness" and ">"

Column 42, Line 55, Claim 49
Please delete "carder" and insert --carrier--

Column 42, Line 56, Claim 49
Please delete "carder" and insert --carrier--

Signed and Sealed this

Fifth Day of August, 2008

JON W. DUDAS
*Director of the United States Patent and Trademark Office*